United States Patent
Nocera, Jr. et al.

(10) Patent No.: US 11,230,613 B2
(45) Date of Patent: *Jan. 25, 2022

(54) RUBBER AND BY-PRODUCT EXTRACTION SYSTEMS AND METHODS

(71) Applicant: Kultevat, Inc., Creve Coeur, MO (US)

(72) Inventors: Anthony Nocera, Jr., Creve Coeur, MO (US); Daniel R. Swiger, Creve Coeur, MO (US)

(73) Assignee: KULTEVAT, INC., Creve Coeur, MO (US)

( * ) Notice: Subject to any disclaimer, the term of this patent is extended or adjusted under 35 U.S.C. 154(b) by 72 days.

This patent is subject to a terminal disclaimer.

(21) Appl. No.: 16/782,301

(22) Filed: Feb. 5, 2020

(65) Prior Publication Data

US 2020/0172637 A1    Jun. 4, 2020

Related U.S. Application Data

(63) Continuation of application No. 16/055,771, filed on Aug. 6, 2018, now Pat. No. 10,584,185.

(60) Provisional application No. 62/542,504, filed on Aug. 8, 2017, provisional application No. 62/551,291, filed on Aug. 29, 2017.

(51) Int. Cl.
| | |
|---|---|
| C08C 1/04 | (2006.01) |
| B01D 11/02 | (2006.01) |
| B01D 11/04 | (2006.01) |
| B01D 15/26 | (2006.01) |
| C07H 1/08 | (2006.01) |
| C08C 1/12 | (2006.01) |
| C08C 1/14 | (2006.01) |

(52) U.S. Cl.
CPC ............ *C08C 1/04* (2013.01); *B01D 11/0257* (2013.01); *B01D 11/0284* (2013.01); *B01D 11/0288* (2013.01); *B01D 11/0296* (2013.01); *B01D 11/0434* (2013.01); *B01D 11/0488* (2013.01); *B01D 11/0492* (2013.01); *B01D 15/26* (2013.01); *C07H 1/08* (2013.01); *C08C 1/12* (2013.01); *C08C 1/14* (2013.01)

(58) Field of Classification Search
USPC ................................................. 528/501, 502
See application file for complete search history.

(56) References Cited

U.S. PATENT DOCUMENTS

| | | | |
|---|---|---|---|
| 3,585,104 A | 6/1971 | Kleinert | |
| 4,046,668 A | 9/1977 | Farcasiu et al. | |
| 4,746,401 A | 5/1988 | Roberts et al. | |
| 9,211,483 B2 | 12/2015 | Merkel et al. | |
| 9,346,924 B2 | 5/2016 | Wade et al. | |
| 9,611,363 B2 | 4/2017 | Swiger et al. | |
| 10,584,185 B2 * | 3/2020 | Nocera, Jr. | ........ B01D 11/0488 |
| 2004/0211723 A1 | 10/2004 | Husain et al. | |
| 2006/0149015 A1 | 7/2006 | Cornish et al. | |
| 2007/0276112 A1 | 11/2007 | Buranov | |
| 2009/0325253 A1 | 12/2009 | Ascon et al. | |
| 2011/0100359 A1 | 5/2011 | North | |
| 2012/0101259 A1 | 4/2012 | Green et al. | |
| 2012/0151826 A1 | 6/2012 | Powell et al. | |
| 2012/0190092 A1 | 7/2012 | Jaquess et al. | |
| 2013/0210102 A1 | 8/2013 | Slupska et al. | |
| 2013/0210103 A1 | 8/2013 | Slupska et al. | |
| 2013/0224816 A1 | 8/2013 | Elliott et al. | |
| 2014/0094630 A1 | 4/2014 | Anton et al. | |
| 2014/0096830 A1 | 4/2014 | Gastaldo et al. | |
| 2014/0106419 A1 | 4/2014 | Bazzana et al. | |
| 2014/0275621 A1 | 9/2014 | Donen et al. | |
| 2014/0288255 A1 | 9/2014 | Martin et al. | |
| 2015/0167238 A1 | 6/2015 | Powell et al. | |
| 2015/0247010 A1 | 9/2015 | Swiger et al. | |
| 2016/0215312 A1 | 7/2016 | Holtzapple et al. | |
| 2019/0233595 A1 | 8/2019 | Hruschka et al. | |

FOREIGN PATENT DOCUMENTS

| | | |
|---|---|---|
| CN | 1398604 A | 2/2003 |
| CN | 102172437 A | 9/2011 |
| CN | 103301206 A | 9/2013 |
| CN | 103920305 B | 12/2015 |
| CN | 106178587 A | 12/2016 |
| CN | 205796604 U | 12/2016 |
| CN | 106362434 A | 2/2017 |
| CN | 106582058 A | 4/2017 |
| CN | 106943768 A | 7/2017 |
| CN | 206334386 U | 7/2017 |
| GT | 197958349 A | 12/1980 |
| WO | 2013192217 A1 | 12/2013 |
| WO | 2017103769 A1 | 6/2017 |
| WO | 2017103775 A1 | 6/2017 |
| WO | 2017103782 A1 | 6/2017 |
| WO | 2018036825 A1 | 3/2018 |

OTHER PUBLICATIONS

International Search Report and Written Opinion for PCT/US2018/045363 dated Oct. 18, 2018.
International Search Report and Written Opinion for PCT/US2018/045371 dated Oct. 29, 2018.

(Continued)

*Primary Examiner* — Terressa Boykin
(74) *Attorney, Agent, or Firm* — Thompson Coburn LLP

(57) ABSTRACT

Systems and methods for extracting useful by-products and natural rubber from non-*Hevea* rubber bearing plants are disclosed.

18 Claims, 13 Drawing Sheets

(56) References Cited

OTHER PUBLICATIONS

Ramirez-Cadavid et al., "Taraxacum Kok-Saghyz (TK): Compositional Analysis of a Feedstock for Natural Rubber and Other Bioproducts", Industrial Crops & Products, May 23, 2017, 17 pages.
WPI, Database Accession No. 2014-C69031 and CN103435720A with English machine translation, 12 pages.
Extended European Search Report and Written Opinion for Application No. 18845274.2 dated Apr. 19, 2021.

\* cited by examiner

RUBBER AND BY-PRODUCT EXTRACTION SYSTEMS AND METHODS

RELATED APPLICATION DATA

This application is a continuation of U.S. application Ser. No. 16/055,771, filed Aug. 6, 2018, which claims the benefit of U.S. Provisional Patent Application No. 62/542,504, filed Aug. 8, 2017, and U.S. Provisional Patent Application No. 62/551,291 filed Aug. 29, 2017, the disclosures of which are hereby incorporated by reference in their entireties.

BACKGROUND

With growing world demand and difficulties with existing rubber plantation monocultures, there is an urgent world need for alternative, less labor-intensive sources of natural rubber as rubber is a strategic material which is irreplaceable in a variety of applications ranging from elastic bands to vehicle tires.

For example, many tires made today use natural rubber latex that is harvested by hand in small cups from Brazilian rubber trees whose bark has been deliberately wounded. A major portion of the latex rubber that is harvested is solidified to solid blocks of bulk rubber and sold as solid rubber to use in numerous commercial applications as stated above. This process has not changed in over a century. This laborious effort is carried out almost exclusively in Southeast Asia, where economic development and environmental costs are increasingly making labor availability and costs more expensive, and the business model less viable.

The monoculture of the *Hevea brasiliensis* tree (i.e., the rubber tree) is susceptible to devastating diseases and blights, which have occurred primarily in its native Brazilian habitat. Additionally, cultivation of *Hevea* has led to a number of environmentally degrading side effects, including the burning of rubberwood for energy needs, and the untreated discharge of latex rubber processing effluents.

World consumption of bulk natural rubber is forecast to increase four percent annually to over 30 million metric tons in 2019, mainly due to the growth in Asian motor vehicle production. China is already the leading world consumer of natural rubber.

Russian dandelion plants (*Taraxacum kok-saghyz*, or TKS) and other rubber bearing non-*Hevea* plants are one alternative source of rubber. Methods for aqueous extraction and separation of both natural rubber and carbohydrate sugar from roots of rubber-bearing dandelion plants have been disclosed in U.S. Pat. Nos. 9,611,363 and 9,346,924.

SUMMARY

In certain embodiments, processing systems for obtaining a carbohydrate-containing liquid and a carbohydrate-depleted biomass solids from a rubber bearing plant comprising: an extraction system comprising a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, at least one of the continuous stirred tank extraction stages in each extraction system having an inlet adapted and configured to receive a liquid solvent, wherein the at least one continuous stirred extraction stage of the extraction system is adapted and configured for receiving biomass and a liquid solvent comprising water, an aqueous solution, or a combination thereof at a temperature of at least about 50° C., wherein the biomass is from a rubber bearing plant of the genus *Taraxacum* or another non-*Hevea* plant, and wherein the extraction system is adapted and configured to mix the biomass with the liquid solvent in a manner such that the extraction system generates the carbohydrate-containing liquid and the carbohydrate-depleted biomass solids; and a solid-liquid separator arranged in fluid communication with a last in series of the continuous stirred tank extraction stages, wherein the separator is adapted and configured for separating the carbohydrate-depleted biomass solids from the carbohydrate-containing liquid are provided.

In certain embodiments, processing systems for obtaining a polar organics fraction and polar compound-depleted biomass solids from a rubber bearing plant comprising: an extraction system comprising a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, at least one of the continuous stirred tank extraction stages in each extraction system having an inlet adapted and configured to receive a liquid solvent, wherein the at least one continuous stirred extraction stage of the extraction system is adapted and configured for receiving carbohydrate-depleted biomass solids and an organic polar solvent liquid, wherein the carbohydrate-depleted biomass solids is from a rubber bearing plant of the genus *Taraxacum* or another non-*Hevea* plant, and wherein the extraction system is adapted and configured to mix the carbohydrate-depleted biomass solids with the organic polar solvent in a manner such that the extraction system generates the liquid polar organics fraction and the polar compound-depleted biomass solids; and a solid-liquid separator arranged in fluid communication with a last in series of the continuous stirred tank extraction stages, wherein the separator is adapted and configured for separating the polar compound-depleted biomass solids from the liquid polar organics fraction are provided.

In certain embodiments, processing systems for obtaining a rubber-containing non-polar solvent fraction and spent biomass solids from a rubber bearing plant comprising: an extraction system comprising a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, at least one of the continuous stirred tank extraction stages in each extraction system having an inlet adapted and configured to receive a liquid organic solvent, wherein the at least one continuous stirred extraction stage of the extraction system is adapted and configured for receiving polar compound-depleted biomass solids and an non-polar organic solvent, wherein the polar compound-depleted biomass solids are from a rubber bearing plant of the genus *Taraxacum* or another non-*Hevea* plant, and wherein the extraction system is adapted and configured to mix the polar compound-depleted biomass solids with the non-polar organic solvent in a manner such that the extraction system generates the rubber-containing non-polar solvent fraction and the spent biomass solids; and a solid-liquid separator arranged in fluid communication with a last in series of the continuous stirred tank extraction stages, wherein the separator is adapted and configured for separating the spent biomass solids from the rubber-containing non-polar solvent fraction are provided.

In certain embodiments, processing systems for obtaining a rubber containing fraction from a rubber bearing plant comprising: (a) a first extraction system adapted and configured: to receive biomass from the plant or parts thereof and a liquid solvent comprising water, an aqueous solution, or a combination thereof; to mix the biomass and liquid solvent at a temperature of at least about 50° C. in a manner such that the first extraction system generates a carbohydrate-containing liquid and a carbohydrate-depleted biomass solids; and to separate the carbohydrate-depleted biomass solids from the carbohydrate-containing liquid; wherein the rubber bearing plant is of the genus *Taraxacum* or is another non-*Hevea* plant; (b) a second extraction system adapted and configured: to receive the carbohydrate-depleted biomass solids from the first extraction system and a organic polar solvent; to mix the carbohydrate-depleted biomass solids with the organic polar solvent in a manner such that the second extraction system generates a liquid polar organics fraction and polar compound-depleted biomass solids; and to separate the liquid polar organics fraction and polar compound-depleted biomass solids; and (c) a third extraction system adapted and configured to: receive the polar compound-depleted biomass solids from the second extraction system and a non-polar organic solvent; to mix the polar compound-depleted biomass solids with the non-polar organic solvent in a manner such that the third extraction system generates a rubber-containing non-polar solvent fraction and spent biomass solids; and to separate the rubber-containing non-polar solvent fraction and spent biomass solids; wherein at least one of the first, second, or third extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, and each extraction system further comprising a solid-liquid separator arranged in fluid communication with a last in series of the continuous stirred tank extraction stages of the respective extraction system, wherein the solid-liquid separator is adapted and configured to separate the carbohydrate-depleted biomass solids, polar compound-depleted biomass solids, or spent biomass solids from the carbohydrate-containing liquid, the liquid polar organics fraction, or the rubber-containing non-polar solvent fraction are provided. In certain embodiments, one or two of the extraction systems in the aforementioned processing system comprise a Soxhlet extractor, an immersion extractor, a counter current immersion extractor, or a percolation extractor.

In certain embodiments, processing systems for obtaining a rubber containing fraction from a rubber bearing plant comprising: (a) a first extraction system adapted and configured: to receive biomass from the plant or parts thereof and an organic polar solvent; to mix the biomass with the organic polar solvent in a manner such that the second extraction system generates a liquid polar organics fraction and polar compound-depleted biomass solids; and to separate the liquid polar organics fraction and polar compound-depleted biomass solids; and (b) a second extraction system adapted and configured to: receive the polar compound-depleted biomass solids from the first extraction system and a non-polar organic solvent; to mix the polar compound-depleted biomass solids with the non-polar organic solvent in a manner such that the second extraction system generates a rubber-containing non-polar solvent fraction and spent biomass solids; and to separate the rubber-containing non-polar solvent fraction and spent biomass solids; wherein at least one of the first or second extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, and each extraction system further comprising a solid-liquid separator arranged in fluid communication with a last in series of the continuous stirred tank extraction stages of the respective extraction system, wherein the solid-liquid separator is adapted and configured to separate the polar compound-depleted biomass solids or spent biomass solids from the liquid polar organics fraction or the rubber-containing non-polar solvent fraction are provided. In certain embodiments, one of the extraction systems in the aforementioned processing system comprise a Soxhlet extractor, an immersion extractor, a counter current immersion extractor, or a percolation extractor.

In certain embodiments, methods for extracting carbohydrate-containing liquid from a rubber bearing plant comprising: introducing a liquid solvent comprising water, an aqueous solution, or a combination thereof and biomass from the plant or a part thereof into at least one continuous stirred tank extraction stage of a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, wherein the rubber bearing plant is of the genus *Taraxacum* or is another non-*Hevea* plant; mixing the liquid solvent with the biomass in the at least one continuous stirred tank extraction stage at a temperature of at least about 50° C. to enable the carbohydrates associated with the biomass to be extracted in the liquid solvent; and introducing an effluent from the at least one continuous stirred tank extraction stage into a solid-liquid separator to result in a separated carbohydrate-containing liquid and a carbohydrate-depleted biomass solids are provided.

In certain embodiments, methods for extracting a polar organics fraction from carbohydrate-depleted biomass solids of a rubber bearing plant comprising: introducing an organic polar solvent and the carbohydrate-depleted biomass solids into at least one continuous stirred tank extraction stage of a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, wherein the rubber bearing plant is of the genus *Taraxacum* or is another non-*Hevea* plant; mixing the organic polar solvent with the carbohydrate-depleted biomass solids in the at least one continuous stirred tank extraction stage in a manner to enable the polar organics fraction associated with the solid to be extracted in the organic polar solvent; and introducing an effluent from the at least one continuous stirred tank extraction stage into a solid-liquid separator to result in a separated polar organics fraction liquid and polar compound-depleted biomass solids are provided.

In certain embodiments, methods for extracting a rubber-containing non-polar solvent fraction from polar compound-depleted biomass solids of a rubber bearing plant comprising: introducing an non-polar organic solvent and the polar compound-depleted biomass solids into at least one continuous stirred tank extraction stage of a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, wherein the rubber bearing plant is of the genus *Taraxacum* or is another non-*Hevea* plant; mixing the non-polar organic solvent with the polar compound-depleted biomass solids in the at least one continuous stirred tank extraction stage in a manner to enable the rubber-containing non-polar solvent fraction associated with the solid to be extracted in the non-polar organic solvent; and introducing an effluent from the at least one continuous stirred tank extraction stage into a solid-liquid separator to result in a separated rubber-containing non-polar solvent fraction and spent biomass solids are provided.

In certain embodiments, methods for extracting a rubber-containing non-polar solvent fraction from a rubber bearing plant comprising (a) introducing into a first extraction system biomass from the plant or parts thereof and a liquid solvent comprising water, an aqueous solution, or a combination thereof; mixing the biomass and liquid solvent at a temperature of at least about 50° C. to generate a carbohydrate-containing liquid and a carbohydrate-depleted biomass solids; and separating the carbohydrate-depleted biomass solids from the carbohydrate-containing liquid; wherein the rubber bearing plant is of the genus *Taraxacum* or is another non-*Hevea* plant; (b) introducing into a second extraction system the carbohydrate-depleted biomass solids from the first extraction system an organic polar solvent; mixing the carbohydrate-depleted biomass solids with the organic polar solvent to generate a liquid polar organics fraction and polar compound-depleted biomass solids, and separating the liquid polar organics fraction and polar compound-depleted biomass solids; and, (c) introducing into a third extraction system the polar compound-depleted biomass solids from the second extraction system and a non-polar organic solvent; mixing the polar compound-depleted biomass solids with the non-polar organic solvent to generate a rubber-containing non-polar solvent fraction and spent biomass solids; and separating the rubber-containing non-polar solvent fraction and spent biomass solids; wherein at least one of the first, second, or third extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, and each extraction system further comprising a solid-liquid separator arranged in fluid communication with a last in series of the continuous stirred tank extraction stages of the respective extraction system, wherein the solid-liquid separator is adapted and configured to separate the carbohydrate-depleted biomass solids, polar compound-depleted biomass solids, or spent biomass solids from the carbohydrate-containing liquid, the liquid polar organics fraction, or the rubber-containing non-polar solvent fraction are provided. In certain embodiments of the aforementioned methods, one or two of the extraction systems comprise a Soxhlet extractor, an immersion extractor, a counter current immersion extractor, or a percolation extractor.

In certain embodiments, methods for extracting a rubber-containing non-polar solvent fraction from a rubber bearing plant comprising (a) introducing into a first extraction system biomass from the plant or parts thereof and an organic polar solvent; mixing the biomass with the organic polar solvent to generate a liquid polar organics fraction and polar compound-depleted biomass solids, and separating the liquid polar organics fraction and polar compound-depleted biomass solids; wherein the rubber bearing plant is of the genus *Taraxacum* or is another non-*Hevea* plant; (b) introducing into a second extraction system the polar compound-depleted biomass solids from the first extraction system and a non-polar organic solvent; mixing the polar compound-depleted biomass solids with the non-polar organic solvent to generate a rubber-containing non-polar solvent fraction and spent biomass solids; and separating the rubber-containing non-polar solvent fraction and spent biomass solids; wherein at least one of the first or second extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, and each extraction system further comprising a solid-liquid separator arranged in fluid communication with a last in series of the continuous stirred tank extraction stages of the respective extraction system, wherein the solid-liquid separator is adapted and configured to separate the polar compound-depleted biomass solids or spent biomass solids from the liquid polar organics fraction or the rubber-containing non-polar solvent fraction are provided.

DETAILED DESCRIPTION

Definitions

Figure 1:
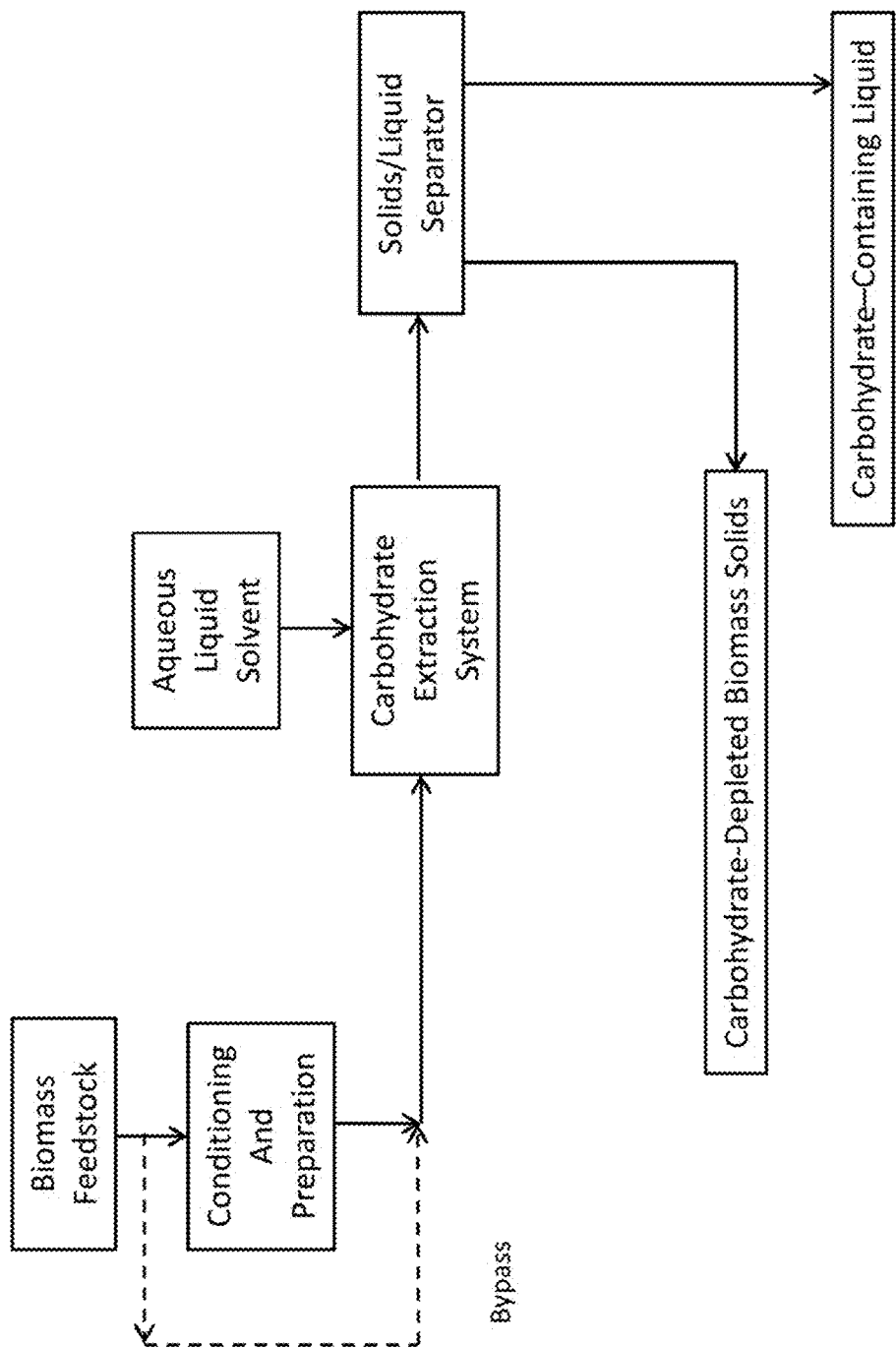
FIG. 1 is a schematic diagram of the process steps for extracting biomass feedstock to obtain carbohydrate-depleted biomass solids and a carbohydrate containing liquid.

As used herein, the terms "biomass" or "biomass feedstock" refer to any or all parts of a non-*Hevea* rubber bearing plant (e.g. a plant of the genus *Taraxacum*) as well as to any or all parts of a non-*Hevea* rubber bearing plant (e.g. a plant of the genus *Taraxacum*) that have been subjected to any size reduction, conditioning, and/or preparation. Such biomass or biomass feedstock can be wet or dry.

As used herein, the phrase "carbohydrate-depleted biomass solids" refers to wet or dried solid material obtained by subjecting biomass of a non-*Hevea* rubber bearing plant (e.g. a plant of the genus *Taraxacum*) to an extraction process wherein carbohydrates are extracted from the biomass. Examples of extraction processes for obtaining carbohydrate-depleted biomass solids include, but are not limited to, extraction with liquid solvent comprising water, an aqueous solution, or a combination thereof at a temperature of at least about 50° C. Dried carbohydrate-depleted biomass solids comprises about 10% or less water by weight.

As used herein, the phrases "continuous stirred tank extraction stage" or "CSTE stage" refers to a single continuous stirred tank extraction (CSTE) tank or vessel.

As used herein, the phrase "polar compound-depleted biomass solids" refers to wet or dried solid material obtained by subjecting either biomass or carbohydrate-depleted biomass solids of a non-*Hevea* rubber bearing plant (e.g. a plant of the genus *Taraxacum*) to extraction with an organic polar solvent. A plurality of polar compounds are depleted in the polar compound-depleted biomass solids by extraction of the biomass or carbohydrate-depleted biomass solids. Dried polar compound-depleted biomass solids comprise about 10% or less water by weight.

As used herein, the term "Polydispersity" or the symbol "P" refers to the ratio of the weight-average molar weight (Mw) divided by the number-average molar weight (Mn). Polydispersity (P) is thus equal to Mw/Mn. In certain embodiments, the Mw and Mn values used to obtain Mw/Mn are determined by Gel Permeation Chromatography (GPC) in combination with Evaporative Light Scattering Detection (GPC-ELSD), GPC in combination with Multi-Angle Light scattering (GPC-MALS), and GPC in combination with Refractive Index (GPC-RI). The phrase and acronym "Gel Permeation Chromatography" or "GPC" refer to the same technique as the phrases and acronyms "Size Exclusion Chromatography," "SEC," or "GPC/SEC." The term "Polydispersity" or the symbol "P" thus refer to the same ratio referred to by the terms, phrases, and symbols "Polydispersity Index," "PDI", "Dispersity," "D-stroke," or "D" when those terms, phrases, and symbols refer to a value equal to Mw/Mn, where Mw and Mn are determined by any one or any combination of the aforementioned analytical methods.

As used herein, the phrase "spent biomass solids" refers to wet or dry solid material obtained by subjecting polar compound-depleted biomass solids of a non-*Hevea* rubber bearing plant (e.g. a plant of the genus *Taraxacum*) to extraction with a non-polar organic solvent. Dried spent biomass solids comprise about 0.1% or less non-polar solvent by weight.

As used herein, the phrase "rubber-containing non-polar solvent fraction" refers to natural rubber dissolved in liquid comprising a non-polar organic solvent.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Further Description

Processing systems and methods for production of rubber and by-products from non-*Hevea* plants are provided herein. Benefits of such systems and methods include improvements in the capital cost and profitability of non-*Hevea* plant rubber extraction operations. In certain embodiments, the characteristics, quality, and/or purity of the rubber produced by the provided systems and methods are also improved resulting in additional final product marketing opportunities in comparison to previously disclosed systems and methods. Such rubber bearing non-*Hevea* plants that can be used include, but are not limited to, plants of the genus *Taraxacum*, plants of the genus *Crysothamnus* (e.g., "Rabbit-Brush" or *Crysothamnus nauseousus*), plants of the genus *Asclepias* ("Milkweed" or *Asclepias syriaca*), and plants of the genus *Parthenium* (e.g., "guayule" or *Parthenium argentatum*). Plants of the genus *Taraxacum* include, but is not limited to, *T. koksaghyz* or a cultivar thereof, a variety comprising introgressed germplasm from one or more *Taraxacum* species or cultivars, a variety comprising inter-specific hybrid germplasm, a variety comprising hybrid germplasm from two or more cultivars, a variety arising from mutagenesis or gene-editing of any rubber bearing *Taraxacum* species, cultivars, or variety, a transgenic *Taraxacum* plant, or any combination thereof. A *Taraxacum* variety can in certain embodiments, comprise inter-specific hybrid germplasm of *T. koksaghyz* and *T. officinale*.

Figure 2:
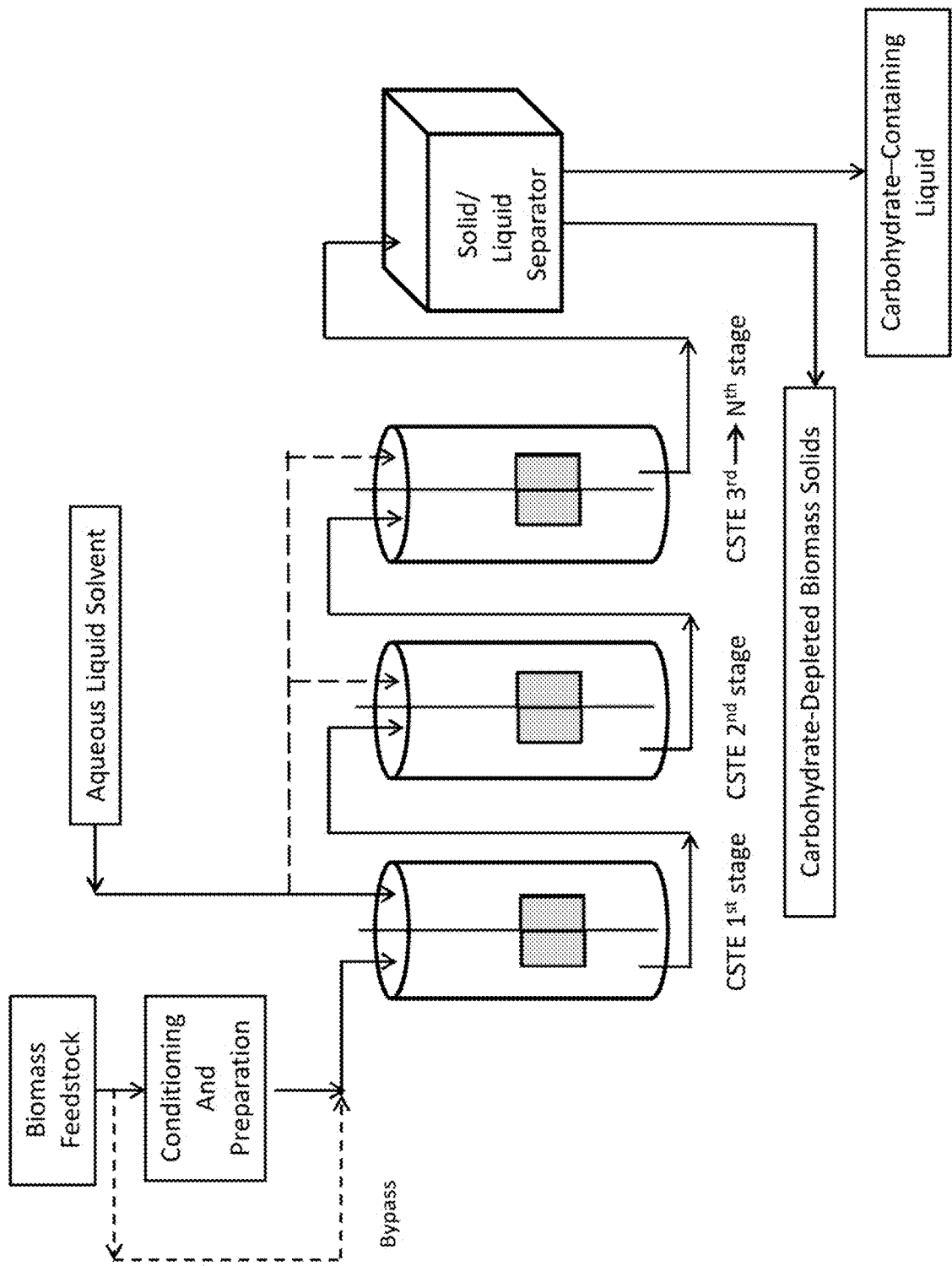
FIG. 2 is a schematic diagram of an exemplary CSTE system for extracting biomass feedstock to obtain carbohydrate-depleted biomass solids and a carbohydrate containing liquid.
Figure 3:
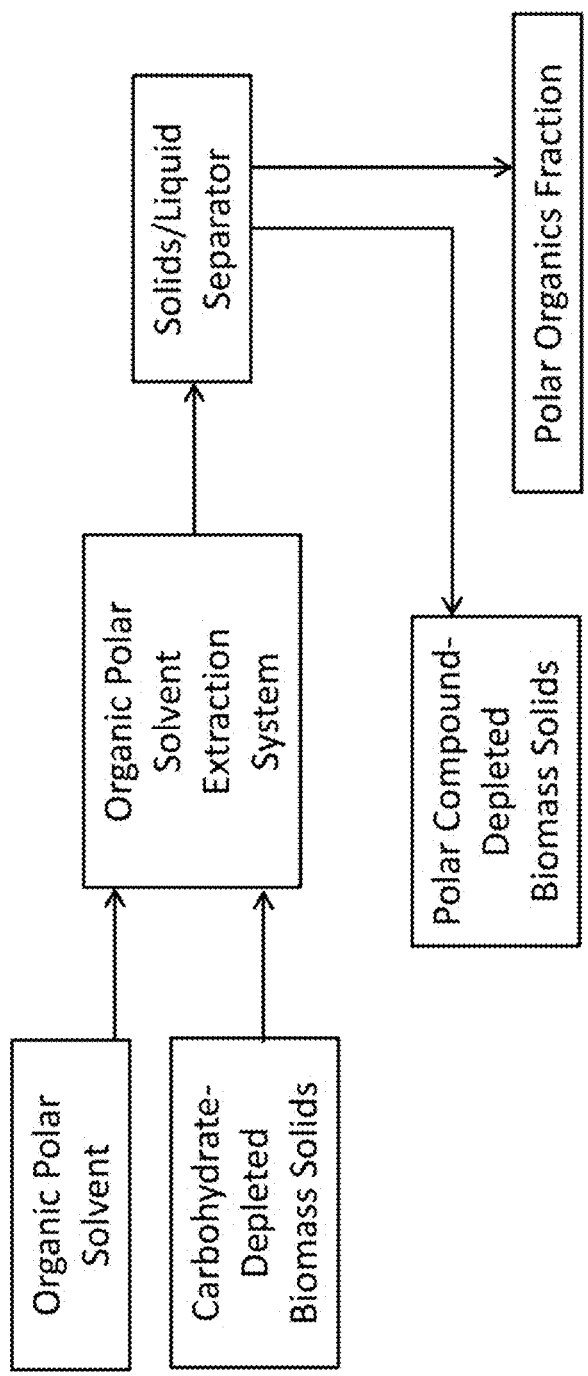
FIG. 3 is a schematic diagram of the process steps for extracting carbohydrate-depleted biomass solids to obtain polar compound-depleted biomass solids and a polar organics fraction.
Figure 4:
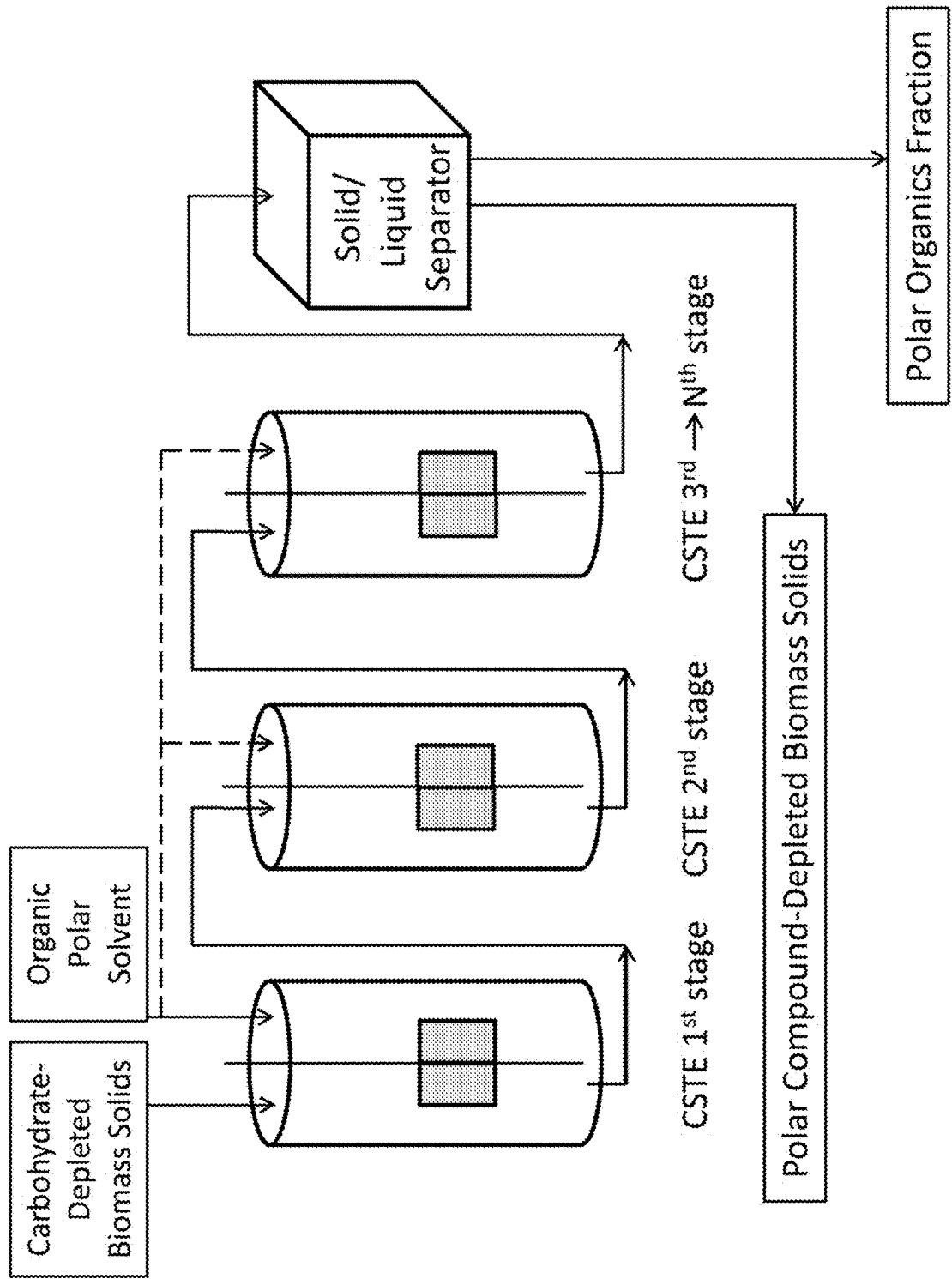
FIG. 4 is a schematic diagram of an exemplary CSTE system for extracting carbohydrate-depleted biomass solids to obtain polar compound-depleted biomass solids and a polar organics fraction.
Figure 5:
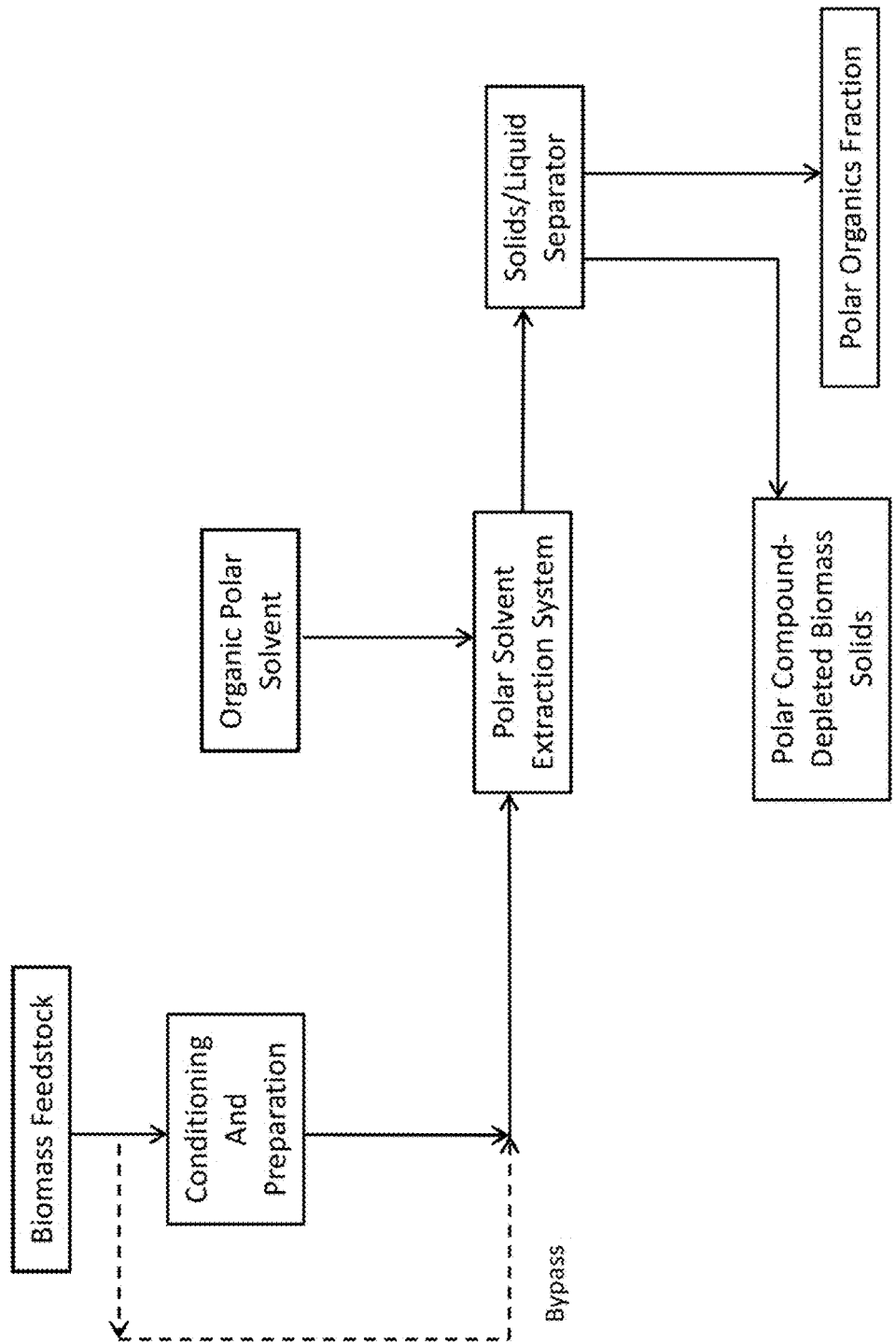
FIG. 5 is a schematic diagram of the process steps for extracting biomass feedstock to obtain polar compound-depleted biomass solids and a polar organics fraction.
Figure 6:
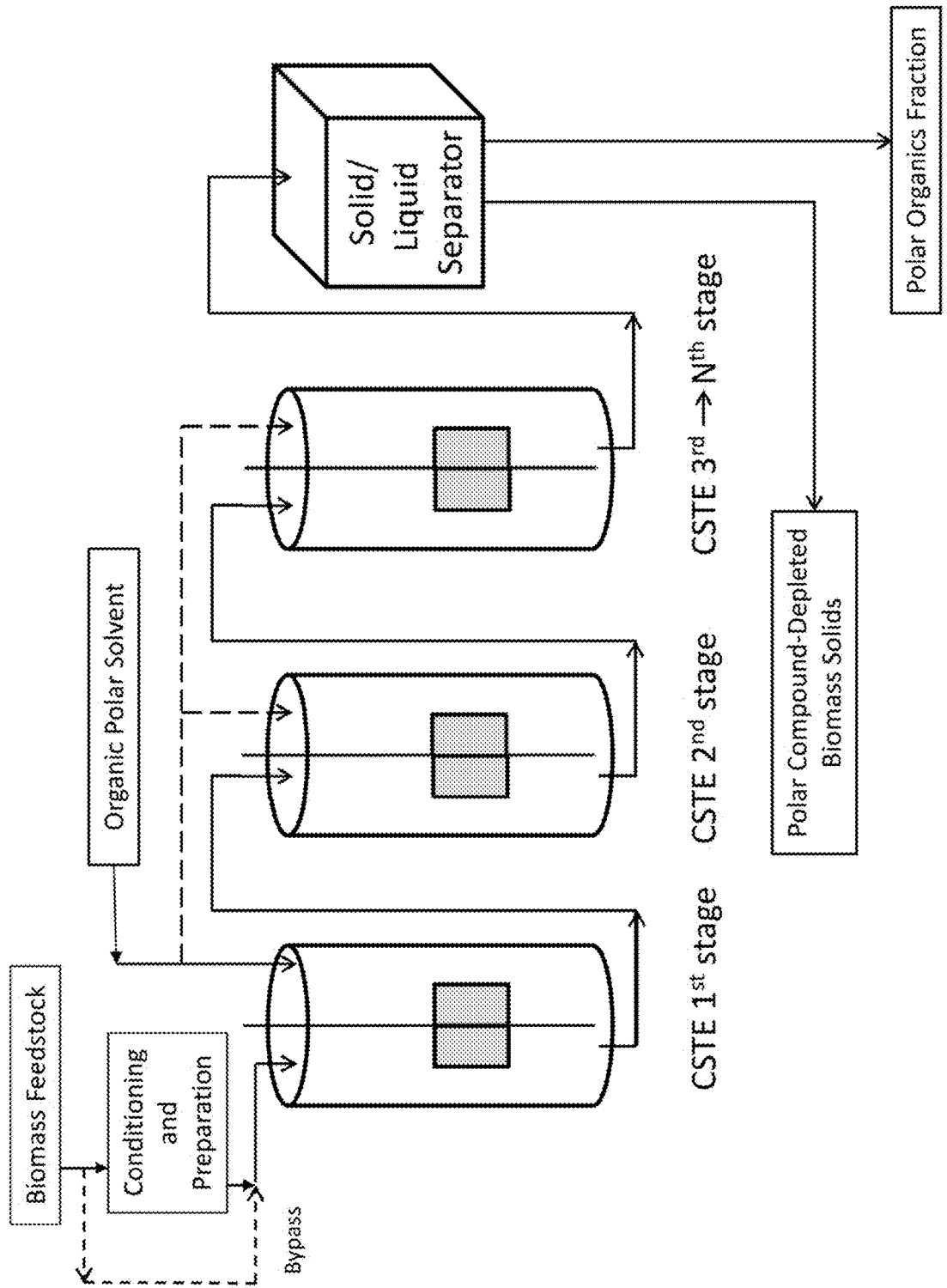
FIG. 6 is a schematic diagram of an exemplary CSTE system for extracting biomass feedstock to obtain polar compound-depleted biomass solids and a polar organics fraction.
Figure 7:
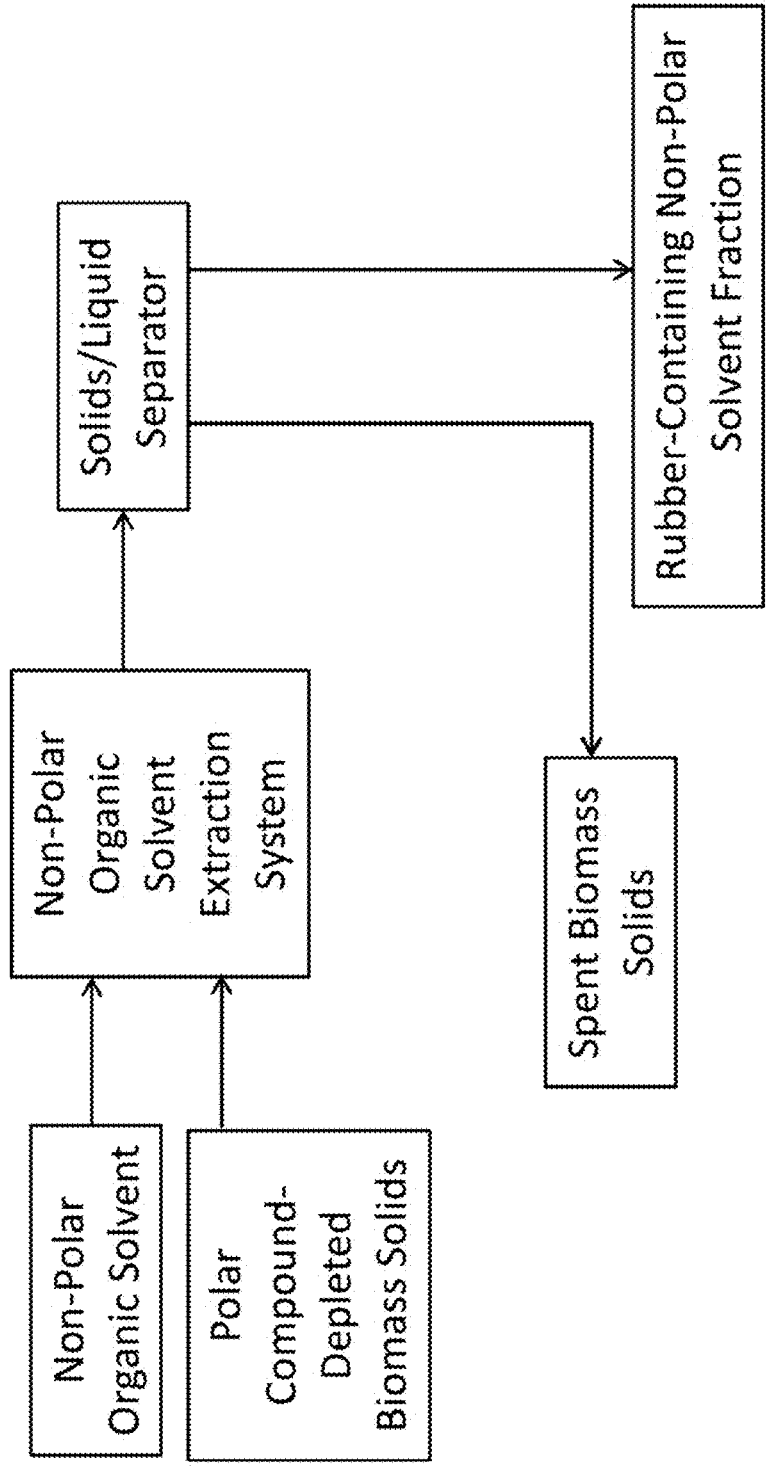
FIG. 7 is a schematic diagram of the process steps for extracting polar compound-depleted biomass solids to obtain spent biomass solids and a rubber containing non-polar solvent fraction.
Figure 8:
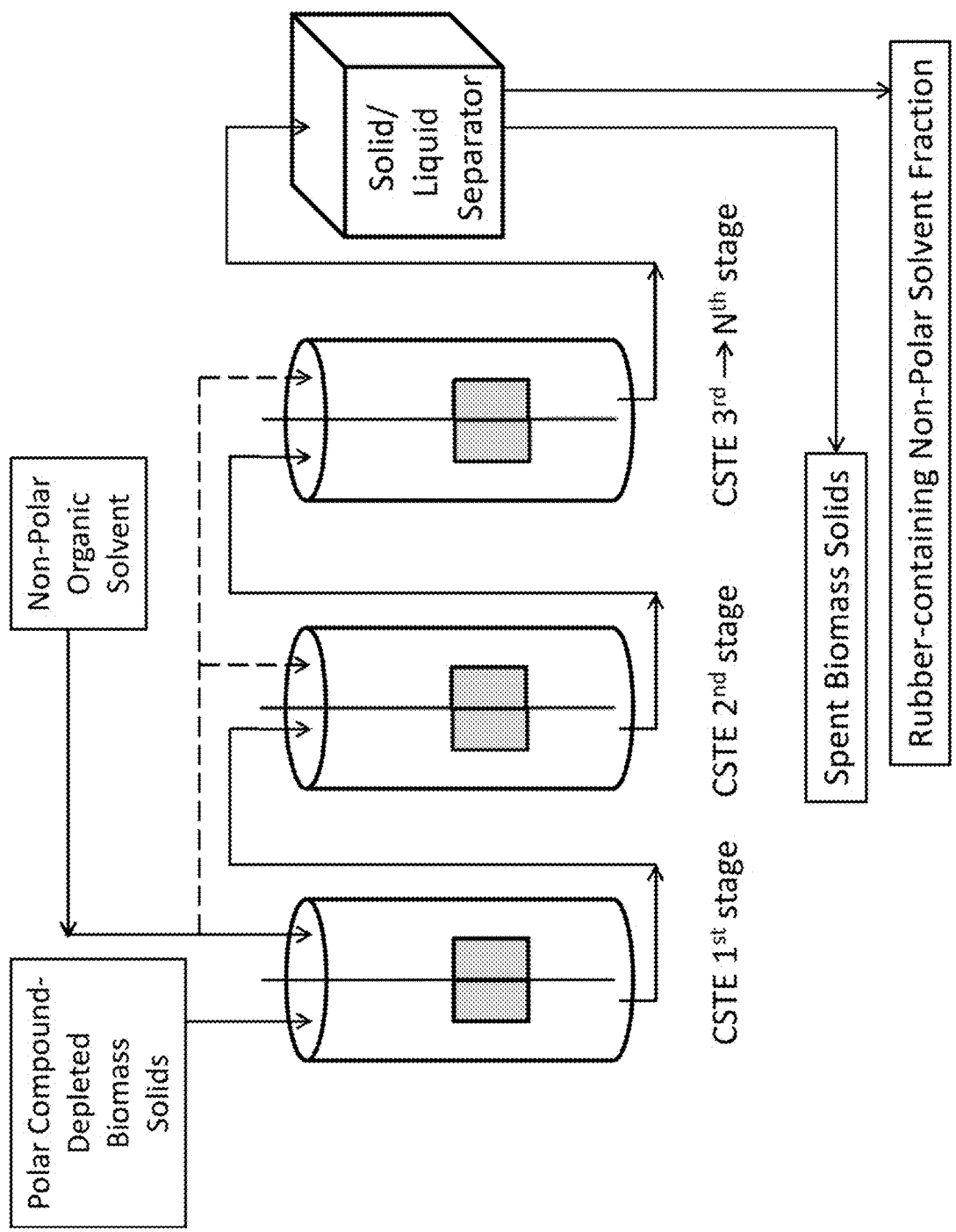
FIG. 8 is a schematic diagram of an exemplary CSTE system for extracting polar compound-depleted biomass solids to obtain spent biomass solids and a rubber containing non-polar solvent fraction.
Figure 9:
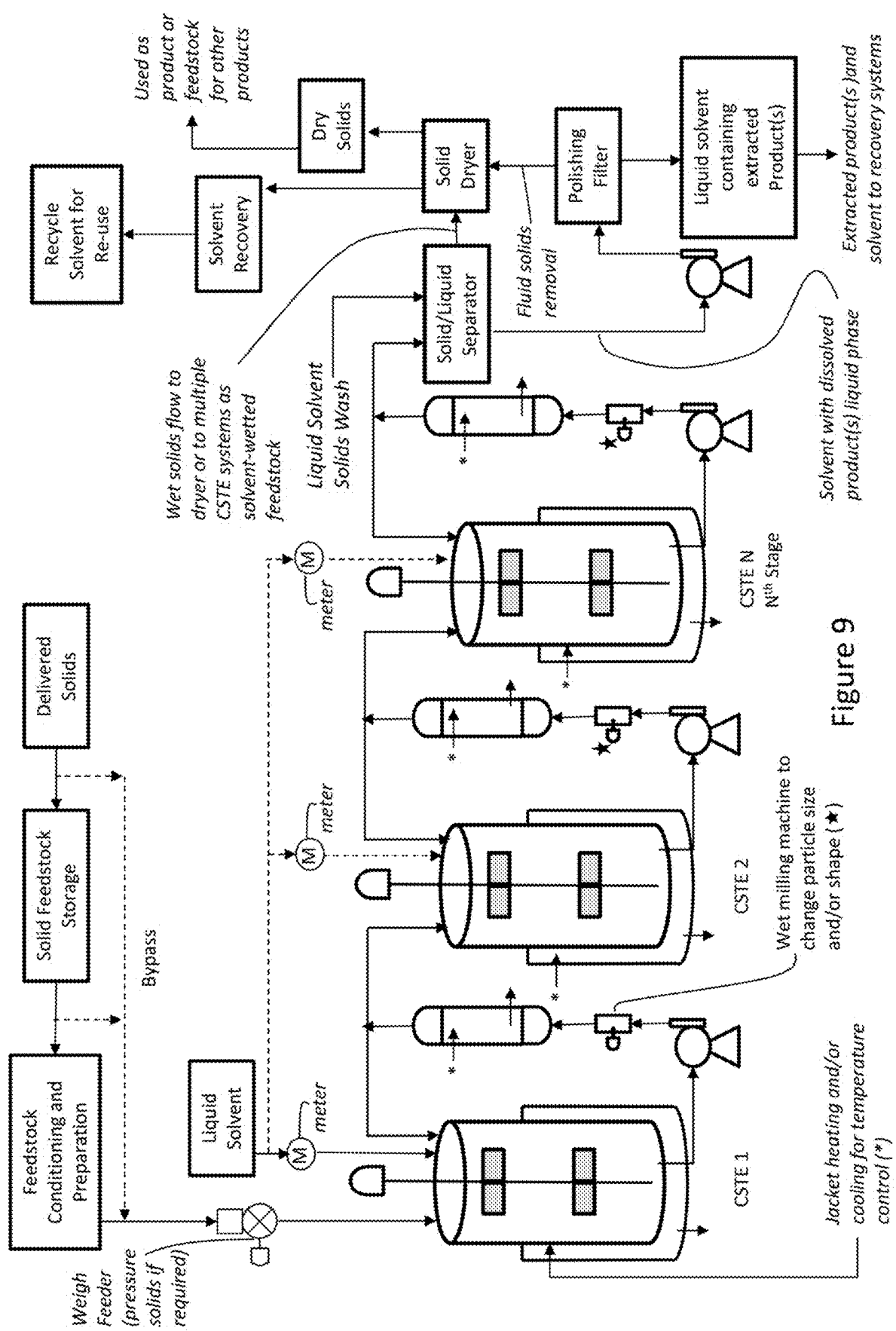
FIG. 9 is a schematic diagram of an exemplary CSTE system comprised of 1 to N stages, a solid liquid separator, a wet solids dryer, product(s) containing liquid and solvent recovery, and product(s) depleted solids drying and solvent recovery.
Figure 10:
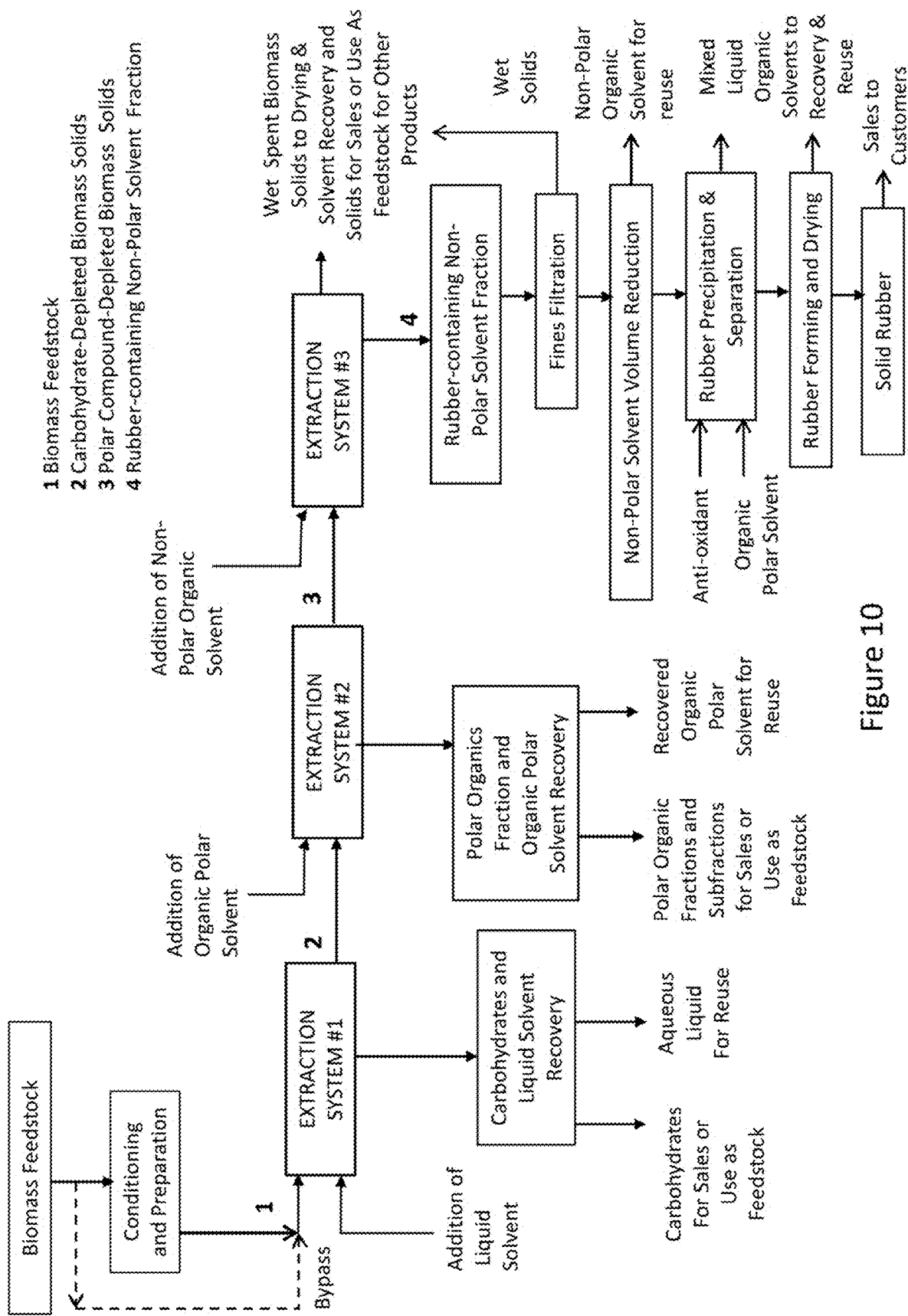
FIG. 10 is a schematic diagram of a process flow for products extraction processing systems and methods with carbohydrate extraction.
Figure 11:
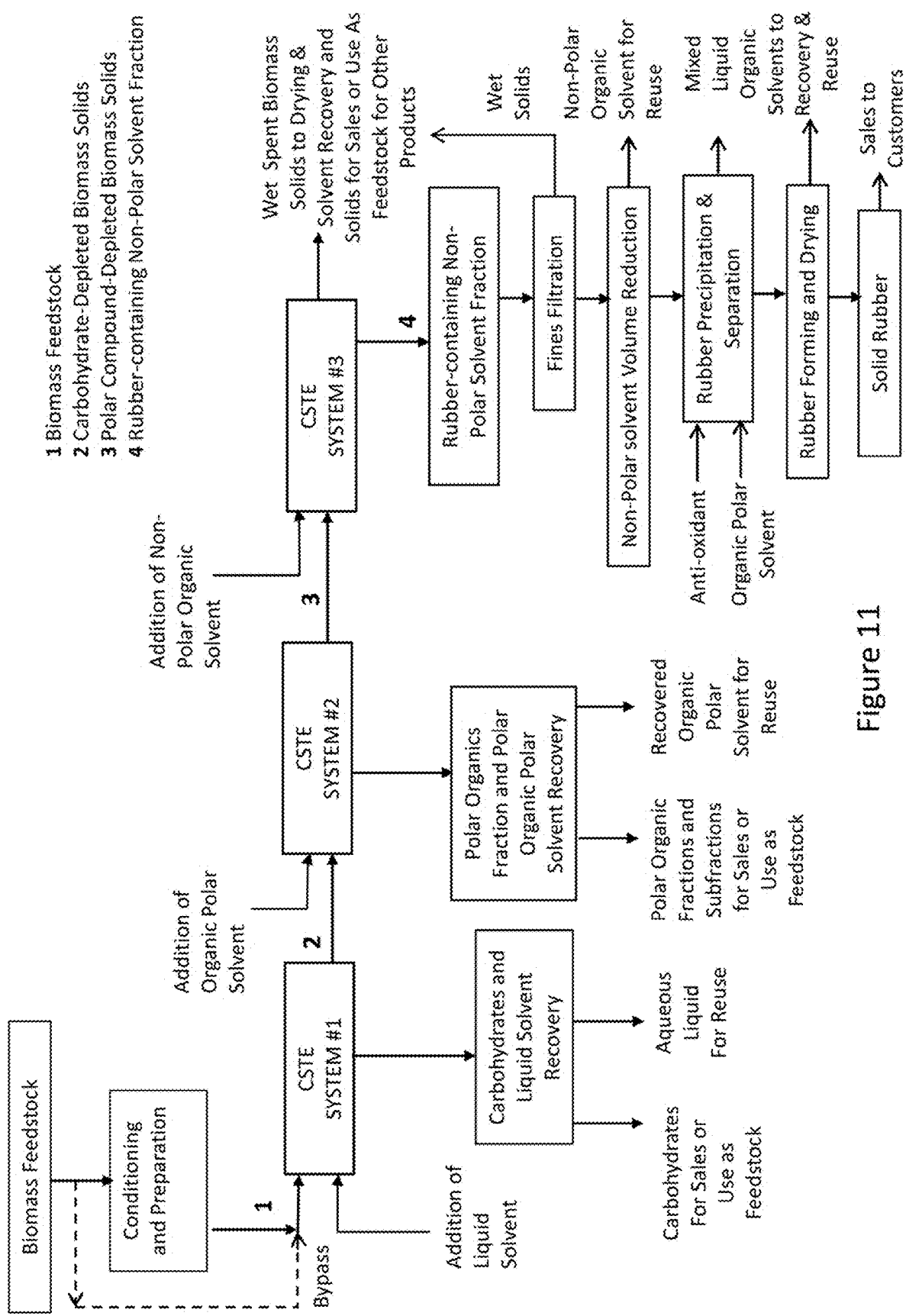
FIG. 11 is a schematic diagram of a process flow for products extraction method with carbohydrate extraction where all of the extraction systems used are CSTE systems.
Figure 12:
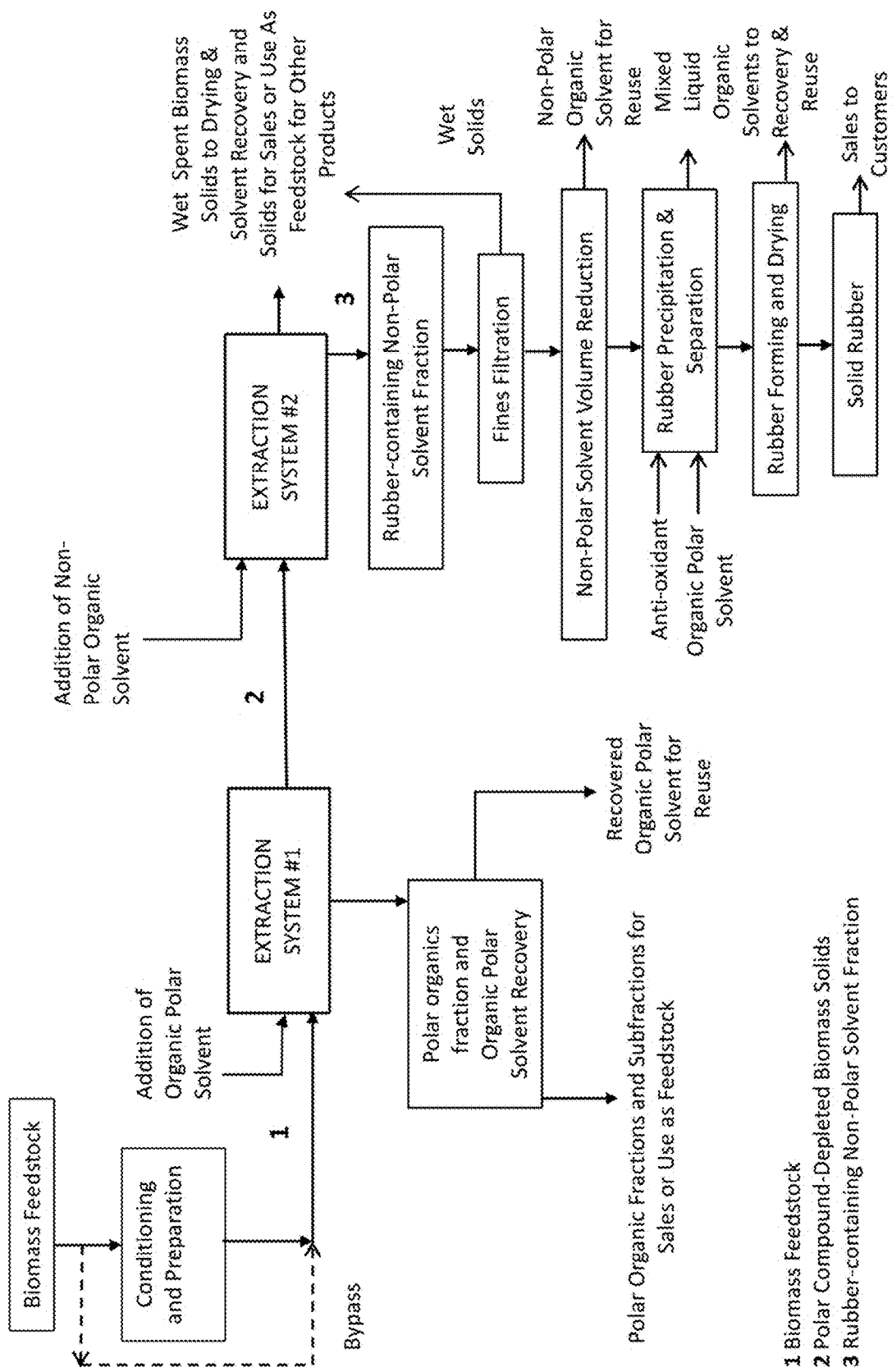
FIG. 12 is a schematic diagram of a process flow for products extraction processing systems and methods without carbohydrate extraction.
Figure 13:
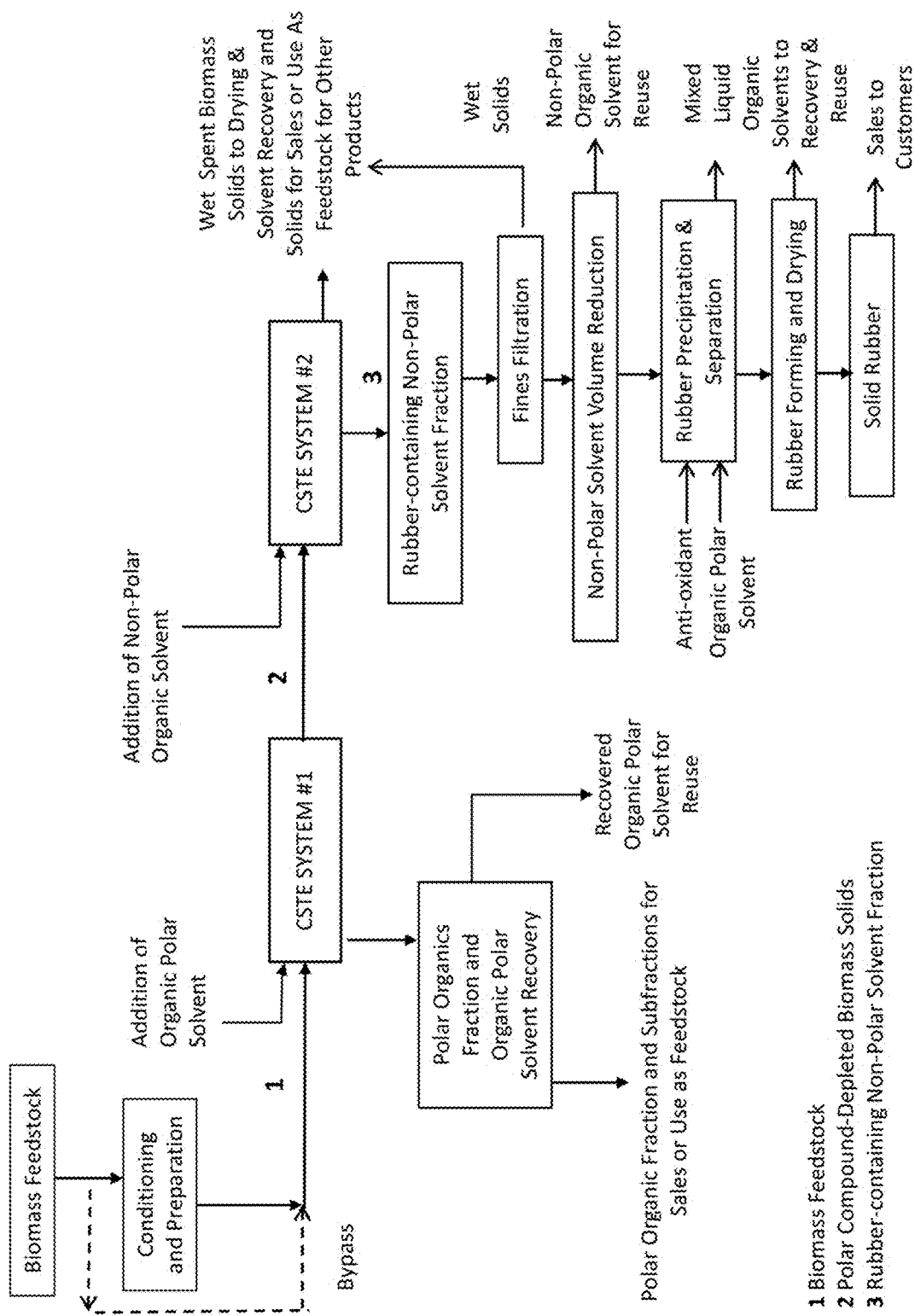
FIG. 13 is a schematic diagram of a process flow for products extraction method without carbohydrate extraction where all of the extraction systems used are CSTE systems.

In certain embodiments, the systems and methods provided herein can extract the by-products and products from biomass feedstock either independently, sequentially, or simultaneously. By-products extracted include carbohydrates (e.g., inulin, fructose, glucose, and the like) and polar organic fractions containing one or more useful compounds (e.g., lubricants, cosmetic ingredients, insect pheromones, sealants, adhesives, surfactants, and emulsifiers). Products extracted include natural rubber (i.e. natural polyisoprene). Non-limiting examples of systems and methods for extracting non-*Hevea* plant biomass feedstock to obtain carbohydrate-depleted biomass solids used in the next extraction as a feedstock for the organic polar solvent extraction and carbohydrate-containing liquid are illustrated in FIGS. 1 and 2. Non-limiting examples of systems and methods for extracting carbohydrate-depleted biomass solids feedstock to obtain polar compound-depleted biomass solids and a polar organics fraction are illustrated in FIGS. 3 and 4. Non-limiting examples of systems and methods for extracting biomass feedstock to obtain polar compound-depleted biomass solids and a polar organics fraction are illustrated in FIGS. 5 and 6. Non-limiting examples of systems and methods for extracting polar compound-depleted biomass solids to obtain spent biomass solids and a rubber-containing non-polar solvent fraction are illustrated in FIGS. 7 and 8. Non-limiting examples of systems and methods for extracting biomass feedstock from non-*Hevea* rubber bearing plants to obtain carbohydrates, polar organics fractions, rubber-containing non-polar solvent fractions, and natural rubber as well as spent biomass for other uses are shown in FIGS. 9, 10, and 11. Non-limiting examples of systems and methods for extracting biomass feedstock from non-*Hevea* rubber bearing plants to obtain polar organics fractions, rubber-containing non-polar solvent fractions, and natural rubber as well as spent biomass for other uses are shown in FIGS. 9, 12, and 13.

In certain embodiments, the feedstock processing systems and methods provide for a continuous process flow of feedstock and selected liquid or solvent through one or more continuous stirred tank extraction (CSTE) stages connected in series. The CSTE stages with the addition of the liquid-solids separator connected in series form a CSTE system. Examples of CSTE systems include, but are not limited to, CSTE systems shown in FIGS. 2, 4, 6, 8, and 9. One or more CSTE systems may be arranged to form the feedstock processing system. In certain embodiments, the systems and methods can comprise a CSTE system adapted and configured to receive wet or dried feedstock (e.g., biomass, carbohydrate extracted biomass solids feedstock, or polar compound-depleted biomass solids feedstocks). In certain embodiments, the systems and methods can comprise a CSTE system adapted and configured to receive wet or dried feedstock (e.g., carbohydrate extracted biomass solids or polar compound-depleted biomass solids feedstocks) from another extraction system or to provide feedstock (e.g., carbohydrate extracted biomass solids, polar compound-depleted biomass solids, spent biomass) to another extraction system. In certain embodiments, the systems and methods can comprise a CSTE system adapted and configured to receive wet or dried feedstock (e.g., biomass, carbohydrate extracted biomass solids, polar compound-depleted biomass solids) from a processing and/or conditioning system or from an extraction system or to provide feedstock (e.g. carbohydrate extracted biomass solids, polar compound-depleted biomass solids, spent biomass) to another extraction system. In certain embodiments, one or more of the CSTE stages in the CSTE system can comprise: (i) an inlet adapted and configured to receive the selected liquid or solvent (e.g. an aqueous liquid solvent, organic polar solvent, or non-polar organic solvent); (ii) an inlet adapted and configured to receive the biomass, the carbohydrate-depleted biomass solids, or the polar compound-depleted biomass solids; or (iii) a combination of an inlet of (i) and an inlet of (ii). In certain embodiments, one or more of the CSTE stages in the CSTE system can comprise a single inlet adapted and configured to receive both the selected liquid or solvent (e.g., an aqueous liquid solvent, organic polar solvent, or non-polar organic solvent) and the biomass, the carbohydrate-depleted biomass solids, or the polar compound-depleted biomass solids. Other extraction systems that can provide feedstock for a CSTE system or that can receive feedstock from a CSTE system can comprise another extraction system, another CSTE system, a Soxhlet extractor, an immersion extractor, a counter current immersion extractor (e.g., Crown Iron Works Model IV, Crown Iron Works Company, Roseville, Minn., USA;), and/or a percolation extractor (e.g., Crown Iron Works Model III or V, Crown Iron Works Company, Roseville, Minn., USA). As used herein, the phrases "immersion extractor," "counter current immersion extractor," and "percolation extractor" are used generically to refer to any method or system that employs any one or more of the immersion, counter-current, and/or percolation-based procedures for extraction of a solid with a solvent. As such, devices including, but not limited to, the "REFLEX®," "LM™ Extractor," or "LLL" devices (Desmet Ballestra, Paris, France), Sliding Cell Extractor or "Lurgi" devices (Air Liquide Engineering and Construction, Paris, France), or any of the aforementioned Crown Iron Works Company devices can be used to provide immersion, counter-current, and/or percolation-based procedures for extraction of a solid with a solvent.

Generally speaking, the systems and methods for extracting useful target products (e.g., by-products such as carbohydrates or polar organic compounds and products such as natural rubber from the solid biomass feedstock, carbohydrate extracted biomass solids, polar compound-depleted biomass solids, spent biomass) in accordance with the principles of the disclosure comprise:

(i) Solids Conditioning & Preparation—In order to extract both the target product on the surface of the biomass feedstock solids, and the product held within the feedstock solids, the particle size and/or particle shape of feedstock should be reduced and/or altered. The solids comprising the feedstock may be chopped, shredded, milled, crushed, and/or pulverized to expand the surface area and open the solids of the feedstock particles for extraction through exposure and penetration of the selected liquid solvent. Additional conditioning such as soaking, maceration, softening and/or drying of the feedstock can also improve expansion of the surface area of the solids of feedstock for exposure to the liquid solvents and subsequent increased mass transfer for targeted product(s) extraction. Biomass feedstock, carbohydrate-depleted biomass solids, and/or polar compound-depleted biomass solid feedstocks from the non-*Hevea* plants can be reduced in size either prior to use in the methods provided herein or in the course of the methods provided herein (e.g., simultaneously with any of the extraction steps). In certain embodiments, the biomass feedstock is reduced to a mean particle size of about 1-5 millimeters. In certain embodiments, the biomass feedstock is reduced to a mean particle size of about 2 millimeters or less. In certain embodiments, biomass from the non-*Hevea* plant can comprise stems, leaves, flowers, crowns, roots or any combination thereof. In certain embodiments where the non-*Hevea* plant is a *Taraxacum* plant, the biomass feedstock for the methods can comprise crowns and roots or just roots of the *Taraxacum* plants. Such crowns and roots or roots can be reduced in size and/or altered in shape as described above. Biomass feedstock can be subjected to conditioning and preparation as harvested and/or in a partially or completely dried form. In certain embodiments, drying can be carried out at a temperature between a low of about 60.degree. C. to a maximum of 100.degree. C. until the moisture level is reduced to less than 10% by weight. In certain embodiments the dried biomass can be stored in low-humidity chambers at ambient temperatures. In certain embodiments, conditioned and prepared biomass feedstock is fed to the first extraction system through an automatic conveying means, e.g., conveyor, rotary feeder, pneumatic transport.

(ii) Extraction Temperature—By increasing the stirred tank pressure and temperature, the conditions for the solvent extraction efficiency to extract the target products from the conditioned and/or prepared feedstock (e.g., biomass, carbohydrate extracted biomass solids, polar compound-depleted biomass solids feedstocks) substantially increases. The higher operating temperature increases the solubility of the product in the liquid solvent and lowers the viscosity of the dissolved product in the liquid solvent and enables the mass transfer of the conditioned feedstock to be optimized. By placing several CSTE stages in series to form the CSTE system, each CSTE stage may operate at a selected pressure and temperature to enable optimum mass transfer and optimum extraction of target products from the feedstock. By way of example, one or more CSTE stages may be configured to operate at atmospheric pressure using a reflux condenser to minimize the solvent losses. Other CSTE stages may be configured to operate at higher temperatures and pressures in a closed system to obtain the optimum extraction performance and efficiency for a selective solvent extraction of a given feedstock. In such embodiments, temperatures and pressures can be adjusted to minimize degradation of desired by-products (e.g., carbohydrates, non-polar organic compounds) and products (natural rubber). CSTE stages configured to operate at higher temperatures and pressures can be partially isolated from other CSTE stages in the series. CSTE stages configured to operate at higher temperatures and pressures may allow for the elimination of transfer pumps and solvent vapor losses between CSTE stages. This in turn increases the solids to solvent ratio reducing the CSTE stage volumes and allows for a potential economic option of using lower purchased cost solvents. Together with mixing discussed below, operating at the highest allowable temperature given the solubility of the solvent and desired product to be extracted from the feed stock results in improved extraction efficiency performance and lower capital and operating costs.

(iii) Mixing, Agitation & Wet Milling—Mixing inside a CSTE stage is accomplished using internal mechanical agitation and appropriately designed internal mechanical baffling. Mixing with aggressive agitation enables the conditioned solid particles to be uniformly suspended in a homogeneous solution and allows the liquid solvent to efficiently contact and dissolve the surface product and improves the liquid solvent mass transfer for penetration transport into, dissolving the internal product, and the transport of the exiting dissolved product laden liquid solvent from the internal regions of the solid particle. Mixing with aggressive agitation also enables the solvent in a liquid phase slurry to achieve a uniform viscosity, thereby increasing the mass transfer for transport penetration and exiting of the conditioned particle. This in turn increases the solids to solvent ratio, along with increased operating temperature and pressure, as discussed above. Improved mixing at the highest allowable temperature given the solubility of the solvent and desired product to be extracted from the feed stock provides the means to improve the extraction efficiency. Mixing and agitation improves the heat transfer through the CSTE stage wall and heat exchange with a heat exchanger integrally formed therewith. Additionally or in the alternative, heat transfer elements can be designed and installed inside the CSTE stage to maintain the optimum pressure and temperature within the CSTE stage. An external heat exchanger can be provided in a recirculation loop to further control temperature of the contents of the CSTE stage when the heat transfer area of the CSTE stage is not adequate for temperature control on the stage. The liquid slurry can be heated or cooled as necessary through the heat exchanger in the recirculation loop as needed given thermal convection in the CSTE stage and thermal conduction through the CSTE stage wall. Further, additional particle size reduction and/or altering the shape of the feedstock may be provided with the modification of the internal agitation blades to create additional shear, and/or with a wet mill disposed in the recirculation loop. The further reduction of particle size and/or shape of the feedstock may allow for improved extraction efficiency, higher solids to solvent ratio resulting in reduced stage volume, a reduced number of stages, and lower overall cycle time.

(iv) Extraction Solvent—An extraction solvent may be chosen based on the solubility of the product at a CSTE stage's operating temperature and pressure, and must be chemically compatible with the conditioned solid feedstock, and the final selected or target product or products. Many choices of both aqueous and organic solvents may be used effectively with high efficiency. One solvent may be introduced in any stage to allow extraction of targeted product(s) as the feedstock flows through the stages in the CSTE system. In the alternative, two or more solvents may be introduced in any stage to allow extraction of two or more target products as the feedstock flows through the stages in the CSTE system. The solvents may be miscible or immiscible. For immiscible solvent systems, the mixing/agitation can be provided to create a homogeneous emulsified stage for improved extraction efficiency for both solvents. In certain embodiments, commercial scale selection of solvent (s) is based on the feedstock, the target products to be extracted, process design, capital installation cost and projected operating expense. This extraction method allows the flexibility to choose lower cost or for any reason (environmental, safety & hygiene, etc.) more desirable liquid solvents with the opportunity to achieve high product extraction efficiency and product yields.

(v) Cycle Time—Overall cycle time for each stage in the CSTE system may be controlled by balancing the mass flow rate required to make the capacity objectives, the volume of each CSTE stage, and the number of stages to accomplish the extraction efficiency objectives. Each stage may be configured for the specific conditions to optimize the performance and extraction efficiency with the aim of reducing capital investment and lowering operating expenses for the CSTE system and overall feedstock processing system.

The stages are arranged in series and are designed and controlled to optimize and provide a high performance extraction efficiency, product quality and product yield. Each stage is in fluid communication with the next stage in series. By fluid communication, the stages may be configured to receive a liquid, a fluid comprising solid and liquid (for instance, a slurry), or combination thereof from the stage connected therewith. The effluent from a stage may be a product dissolved in a liquid solvent, a fluid comprising mixed solids suspended in a liquid solvent (for instance, a slurry), or combination thereof. The number of stages in series will be designed based on the operating capacity, mass balance flow rates, yield requirements, and optimized operating conditions and cycle times. The CSTE system should be configured to optimize the processing conditions, for instance, feedstock (e.g., biomass, carbohydrate extracted biomass solids, or polar compound-depleted biomass solids feedstocks) conditioning and/or preparation, pressure & temperature, heat transfer, mixing and agitation, and wet milling. The feedstock (e.g., biomass, carbohydrate extracted biomass solids, or polar compound-depleted biomass solids feedstocks) manufacturing and processing system may have any number of CSTE systems comprising any number of stages, depending upon processing objectives and requirements. In certain embodiments, conditioned and prepared solid feedstock (e.g., biomass, carbohydrate extracted biomass solids, or polar compound-depleted biomass solids feedstocks) can be measured or metered into the first stage and any stage thereafter. Simultaneously the liquid solvent, which can be preheated to operating temperature, can also be metered into the first stage or any stage thereafter to form a slurry phase where the solids are completely suspended in the liquid solvent, for instance, in a homogeneous mixture with no stratification within the stage. The agitator and internal agitation blades of the stage can be designed for high, medium or low shear mixing and chopping. In certain embodiments, a wet mill can be placed in a recirculation loop with any stage to further reduce the feed stock particle size and shape. The suspended biomass in the liquid solvent, or slurry can be temperature controlled and transferred from the last stage to the continuous solids separation step.

In accordance with another step of the methods, the depleted solid (e.g., carbohydrate extracted biomass solids, polar compound-depleted biomass solids, spent solids, and the like) can be separated from the liquid solvent. In certain embodiments, the solids are mixed with the solvent, which will resemble a homogeneous slurry. As mentioned above, in the homogeneous slurry, the solids are uniformly dispersed within the liquid with no stratification. The solids mixed with the solvent are then cooled prior to the separation step and may be continuously processed for separation by centrifugation, atmospheric or vacuum filter belt, belt press, automated and non-automated pressure filtration, rotary vacuum precoat filter, dissolved gas flotation, settling or any other solids liquid continuous separation process or equipment. In certain embodiments, the solvent wet solids leaving the separator can be transferred to another extraction system for further extraction with a different solvent. For example, carbohydrate-depleted biomass solids from a liquid-solid separator can be transferred to a distinct extraction system for extraction with a organic polar solvent, and polar compound-depleted biomass solids from a liquid-solid separator can be transferred to a distinct extraction system for extraction with a non-polar organic solvent. In certain embodiments, the solvent wet solids leaving the separator are spent biomass solids and can be transferred for spent biomass processing. The liquid with the dissolved product(s), which may be the target products or an intermediate form of the target product, may be pumped through a polishing filter, for instance, less than 100 microns, to remove suspended fine solids. The solids free liquids with the dissolved product(s) may be then transferred for purification, final product(s) recovery, and solvent recovery. The finished or target product(s) may be packaged, inventoried, and shipped as packaged product(s) or inventoried and shipped by bulk for sales. The recovered solvents may be recycled, thereby reducing the solvent's usage and lowering the manufacturing operating expense.

In accordance with another aspect of the method, the spent biomass can be further processed for re-use. Spent solid biomass from a solids separation step is typically wet with the solvent used during the extraction process. In certain embodiments, the wet spent solids may be dried with solvent collection equipment, and any collected solvent may be purified and for internal recycling or reuse. By way of example, the dried spent biomass may have a BTU content of approximately 7,500 BTU per pound and may be used as feedstock for a boiler to produce utility steam at the facility. The boiler may be equipped to use either natural gas, fuel oil, or other local and economically viable fuel to supplement the energy requirements of the facility. When the facility capacity is large and an excess amount of energy can be produced by burning the spent biomass, high pressure steam can be produced to drive turbines to produce electricity for the facility and for export to a local power grid. Therefore, the method provides an option to use all of the spent biomass to produce heat energy in the form of low, medium, and high pressure steam and electricity to operate the facility and sell the excess to a local power grid. When the boiler is burning biomass, it may produce ash that can be used as a byproduct in road construction, as a concrete additive, insulation for steel manufacturing, building materials, and other applicable markets. Dried spent biomass has other potential markets as an animal feed supplement, cellulose insulation, additive or filler for particle board, soil improvement, building supplies, and other direct sales not currently mentioned. The dried spent biomass can also be feedstock for super critical water decomposition, enzymatic digestion and fermentation to produce biofuels such as ethanol used for gasoline or other chemicals current supplied from petroleum. In summary, the dried spent biomass from the process may be used based on economic viability, and that results in an overall renewable and sustainable continuous process where all elements of the biomass are used to produce numerous products without creating wastes that are an environmental burden and cost impact effecting the profitability of the operation. In certain embodiments, this system is a model of a bio-refinery concept. By way of example, the dried solids can be used for the following applications: (a) Land refill or reclamation; (b) aggregate for landscaping, road construction and building materials; (c) an animal feed supplement, cellulose insulation, additive or filler for particle board, soil improvement, and other direct sales not currently mentioned. The spent biomass can also be feedstock for enzymatic digestion and fermentation to produce biofuels such as ethanol used for gasoline or other chemicals current supplied from petroleum. The spent biomass can also be used as feedstock for super critical water decomposition and conversion to carbohydrate sugars and lignins, the products of which can be used as renewable feedstocks for numerous other products.

In certain embodiments, the systems for the non-*Hevea* plants will be located within an economically feasible radius of several farms that can grow and mechanically harvest the plants. In embodiments where the non-*Hevea* plants are *Taraxacum* plants, the plants are harvested at the farm and the loose soil and dirt is shaken from the roots prior to loading the transportation vehicle. Harvested *Taraxacum* plants have a shoot with leaves attached at the top to a surface crown with the subsoil roots attached at the bottom of the crown. During hot weather, the harvested plants can be water sprayed and surface wetted to prevent plant drying during transportation to the processing facility. The amount of harvest and the transportation to the facility can be defined by the 24 hour capacity of the processing facility.

In certain embodiments, harvested plants can be subjected to washing. Washing can comprise use of fresh and/or recycled water to remove the remaining soil and dirt from the shoots, leaves, crowns, and roots. The wash water can be collected, transferred to a settling system to remove the soil and dirt, and then transferred to a water purification system to recover and recycle this water for any use, including, but not limited to, reuse for all of the process water applications for the manufacturing facility. In embodiments where the non-*Hevea* plants are *Taraxacum* plants, washed *Taraxacum* plants can be transferred to a cutting machine that removes the shoot, flowers, and leaves just above the crown, leaving the crown and roots attached and connected. Shoots, flowers, and leaves exit the machine and can be transferred to a packaging area where the shoots, flowers and leaves can be packaged for dandelion sales. *Taraxacum* shoots, flowers and leaves can be used as feedstock for other products such as dandelion tea, dandelion wine, dandelion coffee, and well as other dandelion products for medicinal and other uses. Methods for obtaining various products from *Taraxacum* leaves, tisane, and roots are disclosed in U.S. Pat. No. 9,611,363, which is incorporated herein by reference in its entirety.

In certain embodiments, the feedstock used in certain systems and methods provided herein is biomass, and the outputs are carbohydrate-depleted biomass solids and carbohydrate-containing liquid products or by-products. Non-limiting examples of such systems and methods are illustrated in FIGS. 1, 2, 10, and 11. *Taraxacum* plant crowns and roots contain 10-40 weight percent water soluble carbohydrates mainly comprised of inulin that is a polymer of fructose and glucose sugars. These carbohydrates are stored by the *Taraxacum* plant as a source of energy and can be recovered, sold and or used as valuable byproducts and or feedstock for numerous marketable applications. An aqueous phase liquid (e.g., water and/or aqueous-solution) solvent extraction of *Taraxacum* plant crowns and roots with removal of the water soluble carbohydrates substantially reduces the amount of biomass and the corresponding capital and installation cost for downstream processing. Non-limiting examples of systems and methods for obtaining carbohydrates and carbohydrate-depleted biomass solids are illustrated in FIGS. 1, 2, 10, and 11. In certain embodiments, the systems used can comprise a conditioning and preparation machine adapted and configured to reduce particle size, and/or alter the shape and condition of the biomass that comprises plants or plant part(s) prior to introduction of that biomass into an extraction system (e.g., at least one continuous stirred tank extraction (CSTE) stage, a CSTE system, a Soxhlet extractor, an immersion extractor, a counter current immersion extractor, or a percolation extractor). In certain embodiments, the methods can comprise an initial conditioning and preparation step for reducing the size and/or altering the shape of the biomass feedstock particle that comprises plants or plant part(s) prior to introduction of that biomass into an extraction system. In certain embodiments, a first high shear, agitated continuous stir tank extractor (CSTE) stage is filled with preheated aqueous liquid at a temperature of about 50 to 100° C. when the stage is operated at atmospheric pressure. In other embodiments, a CSTE stage can be operated at temperatures above 100° C. when the stage is subjected to pressures that are above atmospheric pressure. Non-limiting examples of suitable pressures used when the stage is operated above atmospheric pressure include 15, 150, 300, 600, 900, or more than 1000 PSIG (pounds per square inch gauge). In certain embodiments, at least a first CSTE stage has blades adapted and configured to increase shear to reduce and/or alter the particle size and shape of the biomass. In certain embodiments, the CSTE blades adapted and configured to increase shear to reduce and/or alter the particle size and shape of the biomass are internal agitator blades. A slurry pump for the CSTE can have recirculation with a wet mill that further reduces the particle size of the biomass feedstock (e.g., stems, flowers, leaves, crowns, roots, or any combination thereof). The selection of the slurry pump can also impart shear and reduce and/or alter the particle size. In certain embodiments, biomass from a rubber bearing non-*Hevea* plant are transferred by conveyor to a chopper to cut the biomass into small pieces that are then directly charged at a measured and/or controlled rate into the top of the first high shear CSTE stage to extract the water soluble carbohydrates from the biomass particles. Suitable water soluble chemicals for preventing hydrolysis of the inulin polymerized sugar, improving the wetting characteristics' of the biomass, and to reduce foaming can be added to the aqueous liquid. In certain embodiments, the PH of the solution is controlled on the base side at a PH of above 7 and below 10 using ammonia, ammonia hydroxide, sodium hydroxide, sodium carbonate, potassium hydroxide, any other inorganic base chemicals, and any combination thereof in either a hydrous or anhydrous form. Wettability and/or foaming control can be effected by addition of one or more surfactant(s) to the aqueous phase. The overall residence time and incubation time for this continuous aqueous phase extraction can be controlled by the flow rate of the feedstock and water that is the water to biomass ratio, the volume of each CSTE stage in the system, and the number of CSTE stages connected together co-currently in series. In certain embodiments, total anticipated residence time for this continuous aqueous liquid solvent extraction process is a minimum of 1 hour and a maximum of 6 hours. In certain embodiments, the carbohydrate extraction can result in the removal and yield of a minimum of about 60, 70, 80, 90, or 99 weight percent of all of the water soluble carbohydrates from the input biomass feedstock and/or in the conditioning and/or preparation of the reduced particle size or altered shape biomass feedstock for the downstream solvent extraction methods to recover natural organic chemicals and natural rubber. Without seeking to be limited by theory, it is believed that removal of carbohydrates from the biomass feedstock to produce carbohydrate-depleted biomass solids can provide efficient solvent extraction for the downstream processing of the biomass in certain embodiments. Without seeking to be limited by theory, it is also believed that removal of water soluble organic and inorganic materials additionally improves the quality and purity of the recovered solvent extracted organic compounds and natural rubber in the downstream methods in certain embodiments. The exiting aqueous slurry from the last aqueous extraction system can be continuously transferred with a slurry pump to a continuously operated aqueous solid-liquid separator and the liquids are transferred to a water soluble carbohydrates solution storage tank for purification and concentration to sugar syrup and/or dried to form a solid powder or crystalline solid. A solids-liquid separator used in the systems or methods can be a continuous belt press where the solids are hydraulically pressed to remove the maximum amount of liquid. Continuous centrifuges of many types and configurations, as well as other filtration, settling, and/or floatation processes can be used in any configuration or combination as equipment to separate the carbohydrate depleted biomass solids from the carbohydrate-containing liquid. The carbohydrate depleted biomass solids can be washed with fresh water to remove water soluble carbohydrates and other materials from the exiting carbohydrate depleted biomass solids for yield improvement. Carbohydrates obtained by the aforementioned systems and methods can be used as the renewable carbon feedstock for fermentation processes to produce biofuels or for other chemical processes. By way of a non-limiting example, inulin sugar polymers can be chemically converted by aqueous acidification to their fructose and glucose monomers. In other embodiments, inulin polymers can be chemically converted to hydroxymethylfurfural (HMF; 5-(hydroxymethyl)furfural). HMF is documented in the literature and selected by the US Department of Energy and others as a major renewable building block chemical feedstock for chemical synthesis to produce several commodity volume and specialty chemicals currently supplied primarily from petrochemical feedstocks. Some of the major market applications are for the conversion to 2,5-furandicarboxylic acid (FDCA), which has been proposed as a replacement for terephthalic acid and isothalic acids that are used in the manufacture of polyamides, polyesters, and polyurethanes. FDCA can also be polymerized to manufacture poly(ethylene 2,5-furandicarboxylic acid) (PEF), which is a potential substitute for poly(ethylene terephthalate) (PET). HMF can be converted to 2,5-dimethylfuran (DMF), a liquid that is a potential biofuel with a greater energy content than bioethanol. Hydrogenation gives 2,5-bis(hydroxymethyl)furan. Acid-catalyzed hydrolysis converts HMF into levulinic acid (LA) and to gamma-valerolactone (gVL), with loss of formic acid for both fuel and derivative market applications. Ethyl levulinate (EL), 5-ethoxymethylfurfural (EMF), dimethylfurfural (DMF), 2,5-bis(hydroxymethyl)furan (BHMF), 2,5 diformylfuran (DDF) and numerous other commodity and specialty chemicals can also be synthesized starting from HMF. *Taraxacum* biorenewable feedstock can thus provide many value added new products in the future that are alternatives to existing petroleum market supplied products.

In certain instances, the biomass feedstock used in certain processing systems and methods provided herein is carbohydrate-depleted biomass solids and the outputs are polar compound-depleted biomass solids and polar organic fractions or polar organic subfractions. Non-limiting examples of such systems and methods are illustrated in FIGS. 3, 4, 10, and 11. In certain embodiments, carbohydrate-depleted biomass solids feedstock for the systems and methods can be obtained from any extraction device or system, including, but not limited to, a single continuous stir tank extractor (CSTE) stage, a CSTE system, a Soxhlet extractor, an immersion extractor, a counter current immersion extractor, or a percolation extractor that provides for extraction of the carbohydrates from the biomass. Organic polar solvents that can be used in the processing systems and methods include, but are not limited to, an alcohol having 1 to 8 carbon atoms, a ketone having 3 to 8 carbon atoms, a hydroxy ketone having 3 to 8 carbon atoms, a ketol, an ester having 3 to 8 carbon atoms, or a combination thereof. In certain embodiments, the organic polar solvent comprises acetone or water wet acetone. The overall residence, incubation, and/or cycle time for this continuous organic polar solvent extraction can be controlled by the flow rate of the feedstock and organic polar solvent that is the organic polar solvent to carbohydrate-depleted biomass solids ratio, the volume of each CSTE stage in the system, and the number of CSTE stages connected together co-currently in series. In certain embodiments, total anticipated residence time for this continuous extraction process in a CSTE system is a minimum of 1 hour and a maximum of 8 hours. In certain embodiments, the carbohydrate-depleted biomass solids are extracted with the organic polar solvent for about 1 to about 8 hours. A solid-liquid separator used in the systems or methods can be a continuous belt press where the solids are hydraulically pressed to remove the maximum amount of organic polar solvent. Continuous centrifuges of many types and configurations, as well as other filtration, settling, and/or floatation processes can be used in any configuration or combination as equipment to separate the polar compound-depleted biomass solids from the polar organic fraction. The polar compound-depleted biomass solids can be washed with fresh organic polar solvent to remove additional organic compounds for yield improvement. Any of the aforementioned methods can further comprise filtering fine solids from the liquid polar organics fraction. In certain embodiments, one or more by-product sub-fractions enriched for a lubricant, a cosmetic ingredient, an insect pheromone, a sealant, an adhesive, a surfactant, or an emulsifier can also be obtained from a polar organics fraction. In certain embodiments, the sub-fraction will be enriched for at least one of 18-oxo-nonadecanoic acid, palmitic acid ethyl ester, oleanolic acid, cholecalciferol, 17-hydroxy-9Z-octadecenoic acid, sphingosine, 12-oxo-9-octadecynoic acid, cis-5-tetradecenoylcarnitine, azelaic acid, monoolein, beta-hydroxypalmitic acid, dodecylbenzenesulfonic acid, cis-9-hexadecenoic acid, or an isomer thereof. In certain, embodiments, any of the aforementioned by-product sub-fractions of a polar organic fraction can be obtained by methods including, but not limited to, absorption, adsorption, chromatography (e.g., liquid chromatography), crystallization, distillation, sublimation, and combinations thereof. In certain embodiments, the polar compound-depleted biomass solids are depleted for a polar organic compound that is a lubricant, a cosmetic ingredient, an insect pheromone, a sealant, an adhesive, a surfactant, or an emulsifier that was present in the carbohydrate-depleted biomass solids feedstock. In certain embodiments, the polar compound-depleted biomass solids are depleted for a polar organic compound that is at least one of 18-oxo-nonadecanoic acid, palmitic acid ethyl ester, oleanolic acid, cholecalciferol, 17-hydroxy-9Z-octadecenoic acid, sphingosine, 12-oxo-9-octadecynoic acid, cis-5-tetradecenoylcarnitine, azelaic acid, monoolein, beta-hydroxypalmitic acid, dodecylbenzenesulfonic acid, cis-9-hexadecenoic acid, or an isomer thereof that was present in the carbohydrate-depleted biomass solids feedstock.

In certain instances, the biomass feedstock used in certain processing systems and methods provided herein is biomass and the outputs are polar compound-depleted biomass solids and polar organic fractions or polar organic subfractions. Non-limiting examples of such systems and methods are illustrated in FIGS. 5, 6, 12, and 13. Embodiments of systems and methods where the biomass is subjected to extraction with an organic polar solvent without first extracting carbohydrates are thus provided herein. In certain embodiments, biomass feedstock for the systems and methods can be obtained from any extraction device or system, including, but not limited to, a single continuous stir tank extractor (CSTE) stage, a CSTE system, a Soxhlet extractor, an immersion extractor, a counter current immersion extractor, or a percolation extractor that provides for extraction of the carbohydrates from the biomass. In certain embodiments, at least a first CSTE stage has blades adapted and configured to increase shear to reduce and/or alter the particle size and shape of the biomass. In certain embodiments, the CSTE blades adapted and configured to increase shear to reduce and/or alter the particle size and shape of the biomass are internal agitator blades. A slurry pump for the CSTE can have recirculation with a wet mill that further reduces the particle size of the biomass feedstock (e.g., chopped crowns and roots). In certain embodiments, biomass from a rubber bearing non-*Hevea* plant are transferred by conveyor to a chopper to cut the biomass (e.g., stems, flowers, leaves, crowns, roots, or any combination thereof) into small pieces that are then directly charged at a controlled rate into the top inlet of the first high shear CSTE stage, where the inlet is adapted and configured to receive the small pieces of biomass. Organic polar solvents that can be used in the processing systems and methods include, but are not limited to, an alcohol having 1 to 8 carbon atoms, a ketone having 3 to 8 carbon atoms, a hydroxy ketone having 3 to 8 carbon atoms, a ketol, an ester having 3 to 8 carbon atoms, or a combination thereof. In certain embodiments, the organic polar solvent comprises acetone or water wet acetone. The overall residence, incubation, and/or cycle time for this continuous organic polar solvent extraction can be controlled by the flow rate of the feedstock and organic polar solvent that is the organic polar solvent to biomass ratio, the volume of each CSTE stage in the system, and the number of CSTE stages connected together co-currently in series. In certain embodiments, the biomass is extracted with the organic polar solvent for about 1 to about 8 hours. A solid-liquid separator used in the systems or methods can be a continuous belt press where the solids are hydraulically pressed to remove the maximum amount of organic polar solvent. Continuous centrifuges of many types and configurations, as well as other filtration, settling, and/or floatation processes can be used in any configuration or combination as equipment to separate the polar compound-depleted biomass solids from the polar organic fraction. In certain embodiments, the polar compound-depleted biomass solids can be washed with fresh organic polar solvent to remove additional organic compounds for yield improvement. Any of the aforementioned methods can further comprise filtering fine solids from the liquid polar organics fraction. In certain embodiments, one or more by-product sub-fractions enriched for a lubricant, a cosmetic ingredient, an insect pheromone, a sealant, an adhesive, a surfactant, or an emulsifier can also be obtained from a polar organics fraction. In certain embodiments, the sub-fraction is enriched for at least one of 18-oxo-nonadecanoic acid, palmitic acid ethyl ester, oleanolic acid, cholecalciferol, 17-hydroxy-9Z-octadecenoic acid, sphingosine, 12-oxo-9-octadecynoic acid, cis-5-tetradecenoylcarnitine, azelaic acid, monoolein, beta-hydroxypalmitic acid, dodecylbenzenesulfonic acid, cis-9-hexadecenoic acid, or an isomer thereof. In certain, embodiments, any of the aforementioned by-product sub-fractions of a polar organic fraction can be obtained by methods including, but not limited to, absorption, adsorption, chromatography (e.g., liquid chromatography), crystallization, distillation, sublimation, and combinations thereof. In certain embodiments, the polar compound-depleted biomass solids are depleted for a polar organic compound that is a lubricant, a cosmetic ingredient, an insect pheromone, a sealant, an adhesive, a surfactant, or an emulsifier that was present in the biomass feedstock. In certain embodiments, the polar compound-depleted biomass solids are depleted for a polar organic compound that is at least one of 18-oxo-nonadecanoic acid, palmitic acid ethyl ester, oleanolic acid, cholecalciferol, 17-hydroxy-9Z-octadecenoic acid, sphingosine, 12-oxo-9-octadecynoic acid, cis-5-tetradecenoylcarnitine, azelaic acid, monoolein, beta-hydroxypalmitic acid, dodecylbenzenesulfonic acid, cis-9-hexadecenoic acid, or an isomer thereof that was present in the biomass feedstock.

In certain instances, the biomass feedstock used in certain processing systems and methods provided herein are polar compound-depleted biomass solids and the outputs are the spent biomass solids and rubber-containing non-polar solvent. Non-limiting examples of such systems and methods are illustrated in FIGS. 7, 8, 10, 11, 12, and 13. In certain embodiments, polar compound-depleted biomass solids feedstock for the systems and methods can be obtained from any extraction device or system, including, but not limited to, a single continuous stir tank extractor (CSTE) stage, a CSTE system, a Soxhlet extractor, an immersion extractor, a counter current immersion extractor, or a percolation extractor that provides for extraction of the carbohydrates from the biomass. Non-polar organic solvents that can be used in the processing systems and methods include, but are not limited to, one or more hydrocarbon(s) having 1 to 12 carbon atoms. In certain embodiments, the hydrocarbon(s) is/are selected from the group consisting of alkanes having 4 to 9 carbon atoms, cycloalkanes and having 5 to 10 carbon atoms, alkyl substituted cycloalkanes having 5 to 10 carbon atoms, aromatic compounds having 6 to 12 carbon atoms, and alkyl substituted aromatic compounds having 7 to 12 carbon atoms. Non-polar organic solvents used in the systems and methods can comprise n-hexane, mixed hexanes, cyclohexane, n-pentane, mixed pentanes, 2-methylpentane, 3-methylpentane, 2,3-dimethylbutane, 2-2-dimethylbutane, methylcyclopentane, toluene, xylene, tetrahydrafuran, or a mixture thereof. In certain embodiments, the organic solvent comprises mixed hexanes or n-hexane. The overall residence, incubation, and/or cycle time for this continuous non-polar organic solvent extraction can be controlled by the flow rate of the feedstock and non-polar organic solvent that is the non-polar organic solvent to polar compound-depleted biomass solids ratio, the volume of each CSTE stage in the system, and the number of CSTE stages connected together co-currently in series. In certain embodiments, total anticipated residence time for this continuous extraction process in a CSTE system is a minimum of 1 hour and a maximum of 8 hours. In certain embodiments, the polar compound-depleted biomass solids are extracted with the non-polar organic solvent for about 1 to about 8 hours. In certain embodiments, the polar compound-depleted biomass solids are extracted with the non-polar organic solvent at atmospheric pressure and at a temperature below or at the boiling point of the non-polar organic solvent at atmospheric pressure. In other embodiments, the polar compound-depleted biomass solids are extracted with the non-polar organic solvent at a temperature above the boiling point of the non-polar organic solvent at atmospheric pressure and/or at a pressure that is above atmospheric pressure. A solid-liquid separator used in the systems or methods can be a continuous belt press where the spent biomass solids are hydraulically pressed to remove the maximum amount of non-polar organic solvent. Continuous centrifuges of many types and configurations, as well as other filtration, settling, and flotation processes can be used in any configuration or combination as equipment to separate the spent biomass solids from the non-polar organic fraction. The polar compound-depleted biomass solids can be washed with fresh non-polar organic solvent to remove additional rubber from the solids for yield improvement. In certain embodiments, the separation of the rubber-containing non-polar solvent fraction from the spent biomass solids is effected by centrifugation, filtration, settling, and flotation or a combination thereof. In certain embodiments, the spent biomass is dried. Dried spent biomass is used as a feedstock for a boiler to create heat used as a facility utility and or electrical power, feedstock for biofuel production, an animal feed supplement, cellulose insulation, additive or filler for particle board and laminates, soil improvement, or any combination thereof. In certain embodiments, at least 80%, 85%, 90%, 95%, 97%, 98%, or 99% by dry weight of the natural rubber contained in a biomass feedstock used for the initial or subsequent liquid solvent extractions is extracted in the rubber-containing non-polar solvent fraction. In certain embodiments of any of the aforementioned methods, the methods can further comprise at least one of the following steps of: (a) filtering fine solids from the rubber-containing non-polar solvent fraction; (b) removing by distillation or evaporation at least half of the non-polar solvent while maintain the rubber in solution to obtain a concentrated rubber solution; (c) adding an anti-oxidant to a concentrated rubber solution (e.g., with mixing, stirring, agitating, or the like to distribute the anti-oxidant in the concentrated rubber solution); (d) precipitation of the rubber or anti-oxidant treated rubber by adding a sufficient volume of precooled clean organic polar solvent (e.g., about an equal volume of precooled clean organic polar solvent); (e) further cooling the mixture of the organic polar solvent and non-polar organic solvent and precipitated rubber to form a gelatinous rubber precipitate and a mixed liquid organic solvent. (f) separating and removing the gelatinous rubber precipitate from the mixed liquid organic solvent; (g) forming and/or shaping the gelatinous rubber precipitate and/or further removing a portion of the mixed liquid organic solvent; (h) drying the formed and/or shaped gelatinous rubber precipitate to obtain a dried solid rubber product; or, i) any combination of steps (a)-(h). In certain embodiments, the processing systems can further comprise sub-systems adapted and configured for: (a) filtering fine solids from the rubber-containing non-polar solvent fraction; (b) removing by distillation or evaporation at least half of the non-polar solvent while maintain the rubber in solution to obtain a concentrated rubber solution; (c) adding an anti-oxidant to a concentrated rubber solution (e.g., with mixing, stirring, agitating, or the like to distribute the anti-oxidant in the concentrated rubber solution); (d) precipitation of the rubber or anti-oxidant treated rubber by adding a sufficient volume of precooled clean organic polar solvent (e.g., about an equal volume of precooled clean organic polar solvent); (e) further cooling the mixture of the organic polar solvent and non-polar organic solvent and precipitated rubber to form a gelatinous rubber precipitate and a mixed liquid organic solvent. (f) separating and removing the gelatinous rubber precipitate from the mixed liquid organic solvent; (g) forming and/or shaping the gelatinous rubber precipitate and/or further removing a portion of the mixed liquid organic solvent; (h) drying the formed and/or shaped gelatinous rubber precipitate to obtain a dried solid rubber product; or (i) any combination of steps (a)-(h). Samples of natural rubber have a pronounced polydispersed character which is the distribution and homogeneity of individual polyisoprene polymer molecular weights and or masses in the sample. In certain embodiments of the aforementioned systems and methods where the plant is of the genus *Taraxacum* or is another non-*Hevea* rubber bearing plant and the biomass feedstock is obtained from parts of those plants comprising leaves, stems, flowers, roots, crowns, or a combination thereof, a rubber-containing non-polar solvent fraction, gelatinous rubber precipitate, or dried solid rubber comprises polyisoprene having a weight-average molecular weight of about $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, or $1.8 \times 10^6$ to $3.0 \times 10^6$, $4.0 \times 10^6$, $4.5 \times 10^6$, or $5.0 \times 10^6$ grams per mole (g/mol) and can have at least one of an ash content of less than 0.5%, 0.4%, 0.3%, 0.2%, or 0.1%, by weight, 0.1% to 0.5% by weight, or 0% by weight and/or a nitrogen content of less than 0.5%, 0.4%, 0.3%, 0.2%, or 0,1% by weight, 0.1% to 0.5% by weight, or 0% by weight. In certain embodiments of the aforementioned systems and methods where the plant is of the genus *Taraxacum* or is another non-*Hevea* rubber bearing plant and the biomass feedstock is obtained from parts of those plants comprising leaves, stems, flowers, roots, crowns, or a combination thereof, a rubber-containing non-polar solvent fraction, gelatinous rubber precipitate, or dried solid rubber comprises polyisoprene having an essentially unimodal molecular weight distribution with a Polydispersity, P, (Mw/Mn) of 1.1, 1.2, 1.3, 1.4, 1.5, 1.6, 1.7, 1.8, or 1.9 to 3.5, 3.6, 3.7, 3.8, 3.9, or 4; or with a Polydispersity, P, (Mw/Mn) of about 1.1, 2, 3, or 4 and a weight-average molecular weight of about $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, or $1.8 \times 10^6$ to $3.0 \times 10^6$, $4.0 \times 10^6$, $4.5 \times 10^6$, or $5.0 \times 10^6$ g/mol, where Polydispersity and weight-average molecule weight are determined by an analytical method selected from the group consisting of Gel Permeation Chromatography (GPC) in combination with Evaporative Light Scattering Detection (GPC-ELSD), GPC in combination with multi-angle light scattering (GPC-MALS), and GPC in combination with Refractive Index (GPC-RI). In certain embodiments, any of the aforementioned rubber-containing non-polar solvent fractions, gelatinous rubber precipitate, or dried solid rubber comprises polyisoprene having an essentially unimodal molecular weight distribution with a Polydispersity, P, (Mw/Mn) of 1.1, 1.2, 1.3, 1.4, 1.5, 1.6, 1.7, 1.8, or 1.9 to 3.5, 3.6, 3.7, 3.8, 3.9, or 4; or with a Polydispersity, P, (Mw/Mn) of a Polydispersity, P, (Mw/Mn) of about 1.1, 2, 3, or 4, where Polydispersity is determined by an analytical method selected from the group consisting of GPC-ELSD, GPC-MALS, and GPC-RI. In certain embodiments, any of the aforementioned rubber-containing non-polar solvent fractions, gelatinous rubber precipitate, or dried solid rubber comprises polyisoprene having at least one of an ash content of less than 0.5%, 0.4%, 0.3%, 0.2%, or 0.1% by weight, 0.1% to 0.5% by weight, or 0% by weight and/or a nitrogen content of less than 0.5%. 0.4%, 0.3%, 0.2%, or 0.1% by weight, 0.1% to 0.5% by weight, or about 0% by weight. In certain embodiments of the aforementioned systems and methods where the plant is of the genus *Taraxacum* or is another non-*Hevea* rubber bearing plant and the biomass feedstock is obtained from parts of those plants comprising leaves, stems, flowers, roots, crowns, or a combination thereof, the rubber-containing non-polar solvent fraction, gelatinous rubber precipitate, or dried solid rubber has an ash content of less than 0.5%, 0.4%, 0.3%, 0.2%, or 0.1% by weight, 0.1% to 0.5% by weight, or 0% by weight and a nitrogen content of less than 0.5%, 0.4%, 0.3%, 0.2%, or 0.1% by weight, 0.1% to 0.5% by weight, or 0% by weight. In certain embodiments of the aforementioned systems and methods where the plant is of the genus *Taraxacum* or is another non-*Hevea* rubber bearing plant and the biomass feedstock is obtained from parts of those plants comprising leaves, stems, flowers, roots, crowns, or a combination thereof, the rubber-containing non-polar solvent fraction, gelatinous rubber precipitate, or dried solid rubber can have an ash content of less than 0.5%, 0.4%, 0.3%, 0.2%, or 0.1% by weight, 0.1% to 0.5% by weight, or 0% by weight. In certain embodiments of the aforementioned systems and methods where the plant is of the genus *Taraxacum* or is another non-*Hevea* rubber bearing plant and the biomass feedstock is obtained from parts of those plants comprising leaves, stems, flowers, roots, crowns, or a combination thereof, the rubber-containing non-polar solvent fraction, gelatinous rubber precipitate, or dried solid rubber can have a nitrogen content of less than 0.5%, 0.4%, 0.3%, 0.2%, or 0.1%, 0.1% to 0.5% by weight, or 0% by weight. In certain embodiments of the aforementioned systems and methods where the plant is of the genus *Taraxacum* or is another non-*Hevea* rubber bearing plant and the biomass feedstock is obtained from parts of those plants comprising roots, crowns, or a combination thereof, a rubber-containing non-polar solvent fraction, gelatinous rubber precipitate, or dried solid rubber comprises polyisoprene having a weight-average molecular weight of about $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, or $1.8 \times 10^6$ to $3.0 \times 10^6$, $4.0 \times 10^6$, $4.5 \times 10^6$, or $5.0 \times 10^6$ g/mol and can have at least one of an ash content of less than 0.5, 0.4, 0.3, 0.2%, or 0.1% by weight, 0.1% to 0.5% by weight, or 0% by weight and/or a nitrogen content of less than 0.5%, 0.4%, 0.3%, 0.2%, or 0.1% by weight, 0.1% to 0.5% by weight, or 0% by weight. In certain embodiments of the aforementioned systems and methods where the plant is of the genus *Taraxacum* or is another non-*Hevea* rubber bearing plant and the biomass feedstock is obtained from parts of those plants comprising roots, crowns, or a combination thereof, a rubber-containing non-polar solvent fraction, gelatinous rubber precipitate, or dried solid rubber comprises polyisoprene having an essentially unimodal molecular weight distribution with a Polydispersity, P, (Mw/Mn) of 1.1, 1.2, 1.3, 1.4, 1.5, 1.6, 1.7, 1.8, or 1.9 to 3.5, 3.6, 3.7, 3.8, 3.9, or 4; or with a Polydispersity, P, (Mw/Mn) of about 1.1, 2, 3, or 4 and a weight-average molecular weight of about $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, or $1.8 \times 10^6$ to $3.0 \times 10^6$, $4.0 \times 10^6$, $4.5 \times 10^6$, or $5.0 \times 10^6$ g/mol, where Polydispersity and weight-average molecular weight are determined by an analytical method selected from the group consisting of GPC-ELSD, GPC-MALS, and GPC-RI. In certain embodiments, any of the aforementioned rubber-containing non-polar solvent fractions, gelatinous rubber precipitate, or dried solid rubber comprises polyisoprene having an essentially unimodal molecular weight distribution with a Polydispersity, (Mw/Mn) of 1.1, 1.2, 1.3, 1.4, 1.5, 1.6, 1.7, 1.8, or 1.9 to 3.5, 3.6, 3.7, 3.8, 3.9, or 4; where Mw and Mn are determined by an analytical method selected from the group consisting of GPC-ELSD, GPC-MALS, and GPC-RI. In certain embodiments, any of the aforementioned rubber-containing non-polar solvent fraction, gelatinous rubber precipitate, or dried solid rubber comprise polyisoprene having a weight-average molecular weight of about $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, or $1.8 \times 10^6$ to $3.0 \times 10^6$, $4.0 \times 10^6$, $4.5 \times 10^6$, or $5.0 \times 10^6$ g/mol and can have at least one of an ash content of less than 0.5%, 0.4%, 0.3%, 0.2%, or 0.1% by weight, 0.1% to 0.5% by weight, or 0% by weight and/or a nitrogen content of less than 0.5%, 0.4%, 0.3%, 0.2%, 0.1%, or 0% by weight. In certain embodiments, any of the aforementioned rubber-containing non-polar solvent fractions, gelatinous rubber precipitate, or dried solid rubber comprise polyisoprene having at least one of an ash content of less than 0.5%, 0.4%, 0.3%, 0.2%, or 0.1% by weight, 0.1% to 0.5% by weight, or 0% by weight and/or a nitrogen content of less than 0.5%, 0.4%, 0.3%, 0.2%, 0.1%, or 0% by weight. In certain embodiments of the aforementioned systems and methods where the plant is of the genus *Taraxacum* or is another non-*Hevea* rubber bearing plant and the biomass feedstock is obtained from parts of those plants comprising roots, crowns, or a combination thereof, a rubber-containing non-polar solvent fraction, gelatinous rubber precipitate, or dried solid rubber that comprises polyisoprene can have a weight-average molecular weight of about $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, or $1.8 \times 10^6$ to $3.0 \times 10^6$, $4.0 \times 10^6$, $4.5 \times 10^6$, or $5.0 \times 10^6$ g/mol. In certain embodiments of the aforementioned systems and methods where the plant is of the genus *Taraxacum* or is another non-*Hevea* rubber bearing plant and the biomass feedstock is obtained from parts of those plants comprising roots, crowns, or a combination thereof, the rubber-containing non-polar solvent fraction, gelatinous rubber precipitate, or dried solid rubber can have a nitrogen content of less than 0.5%, 0.4%, 0.3%, 0.2%, or 0.1% by weight, or 0% by weight. The dried solid natural rubber produced by the systems and methods provided herein can be used to manufacture a variety of goods that include, but are not limited to, tires.

In certain embodiments, systems and methods provided herein for obtaining a carbohydrate containing liquid, a polar organics fraction, and/or a rubber containing fraction from a rubber bearing non-*Hevea* plant can be fully continuous from the beginning to the end. However, certain sub-processes or step(s) in the aforementioned methods can be operated in the batch mode making the entire process semi-continuous. In certain embodiments, the continuous processing systems and methods can operate for 24 hours per day and seven days per week for a manufacturing campaign that is scheduled for several consecutive weeks. In still other embodiments, the processing systems and methods provided herein are performed in batch mode. In still other embodiments, the processing systems and methods can operate independently of one another.

EXAMPLES

Example 1. *Taraxacum* Plant Harvest, Feedstock Conditioning and/or Preparation, by-Product Extraction, and Product Extraction Receipt of Feedstock The processing facility for *Taraxacum* plant will be located within an economically feasible radius of several farms that will grow and mechanically harvest the *Taraxacum* plants. Mature *Taraxacum* plants are harvested at the farm and the loose soil and dirt is shaken from the roots prior to loading the transportation vehicle. The *Taraxacum* harvested plants can have a shoot, flowers with leaves attached to the top surface of the crown with the subsoil roots attached at the bottom of the crown. During hot weather, the harvested plants can be water sprayed and surface wetted to prevent plant drying during transportation to the processing facility. The vehicle type is either an open top flatbed container to load the container with a front end loader and with a hydraulic lift to dump the contents of the container on a flat unloading area at the facility or the harvested biomass can be compacted using a cotton bailer or similar machine and the bails are loaded onto the vehicle to reduce transportation costs to the processing facility. These vehicle containers can be covered with a tarp to prevent spillage and protection from the weather during transportation. The amount of harvest and the transportation to the facility is defined by the 24 hour capacity of the processing facility.

Processing Facility Feedstock Storage and Preparation

The trucks entering the secured processing facility will first be weighed on the facility vehicle scale and then drive to the unloading staging area. The trucks will be directed to unload the wet *Taraxacum* plants at the unloading staging and storage area and then drive to the truck scale for the empty tare weight. The net weights and biomass feedstock inventory are used by manufacturing operations for process metrics and production scheduling.

The wet *Taraxacum* plants are loaded onto a conveyor, and the conveyor transfers the wet plants to a shaker that removes loose dirt from the plant roots. A magnet and metal detector is located after the shaker to detect and remove metals that can be present in the harvested plants. These metals must be removed prior to further processing to prevent damage and unanticipated downtime to the downstream processing equipment.

Water Soluble Carbohydrates & Materials Removal

The conveyor transfers the wet *Taraxacum* plants to a washing area where both fresh and recycled water are used to remove the remaining soil and dirt from the shoots, flowers, leaves, crowns, and roots. The wash water is collected, transferred to a settling system to remove the soil and dirt, and then transferred to a water purification system to recover and then recycle this water for reuse for all of the process water applications for the facility.

The conveyor transfers the washed *Taraxacum* plants to a cutting machine that removes the shoot, flowers, and leaves just above the crown, leaving the crown and roots attached and naturally connected. The shoots, flowers, and leaves exit the machine and are transferred to a packaging area where the shoots, flowers, and leaves are packaged for dandelion sales. The option exists to ship the shoots, flowers, and leaves in bulk to a processing facility as feedstock for other products such as dandelion tea, dandelion wine, dandelion coffee, and well as other dandelion products for medicinal and other uses. Examples of methods for obtaining various products from *Taraxacum* leaves that can be used are disclosed in U.S. Pat. No. 9,611,363, which is incorporated herein by reference in its entirety. The crowns and roots can be conditioned and prepared for subsequent storage and/or extraction by drying, chopping, shredding, milling, crushing, and/or pulverization. Additional conditioning such as soaking, maceration, and/or softening of the crowns and roots can also be performed.

The first high shear agitated CSTE stage is filled with preheated hot water at a temperature of 50 to 100 C. The slurry pump for the mixing CSTE stage has a recirculation with a wet mill that further reduces the particle size of the chopped crowns and roots. The washed wet *Taraxacum* crowns and roots are transferred by conveyor to a chopper to cut the crowns and roots into small pieces that are then directly charged at a measured and/or controlled rate into the biomass-receiving top inlet of the first high shear CSTE stage to extract the water soluble carbohydrates from the biomass slurry. Chemicals are added to prevent hydrolysis of the natural Inulin polymerized sugar, to improve the wetting characteristics' of the biomass, and to reduce foaming. The PH of the solution is controlled on the base side at a PH of above 7 and below 10 using anhydrous ammonia, ammonia hydroxide, sodium hydroxide, sodium carbonate, potassium hydroxide, any other inorganic base chemicals, and any combination thereof. The overall residence time, incubation, and/or cycle time for this continuous aqueous phase extraction is controlled by the flow rate of the feedstock and water that is the water to biomass ratio, the volume of each CSTE stage in the system, and the number of well stirred and agitated CSTE stages controlled at operating temperatures between 50 C and 100 C connected together co-currently in series. The total anticipated residence time for this continuous aqueous extraction process is a minimum of 1 hour and a maximum of 6 hours. The overall objective of this processing step is the removal and yield of a minimum of 90 weight percent of all of the water soluble carbohydrates and the preparation of the reduced particle size biomass for the downstream solvent extraction processes to recover natural organic chemicals and natural rubber. This process reduces the mass and opens the fibers in the carbohydrate-depleted biomass solids to enable an extremely efficient liquid solvent extraction for recovery of soluble products and by products. The aqueous removal of water soluble organic and inorganic materials additionally improves the quality of the recovered solvent extracted natural organic by-products and the natural rubber product in the downstream processes.

The exiting aqueous slurry from the last aqueous extraction mixing tank or stage is continuously transferred with a slurry pump to a continuously operated aqueous solid-liquid separator and the liquids are transferred to a water soluble carbohydrates solution storage tank for purification and concentration to sugar syrup or drying to form a powder or crystalline solid. The water wet carbohydrate-depleted biomass solids are transferred by conveyor to either the drying step for dried inventory or the second step of the solvent extraction process. The solids-liquid separator can be a continuous belt press where the carbohydrate-depleted solids are hydraulically pressed to remove the maximum amount of liquid. Continuous centrifuges of many types and configurations, as well as other filtration, settling, and flotation processes can be used in any configuration or combination as equipment to complete this process. The exiting carbohydrate-depleted biomass solids can be washed with fresh water to remove water soluble carbohydrates for yield improvement and other water soluble materials that could cause contamination of downstream products and byproducts from the exiting carbohydrate-depleted biomass solids feedstock to the downstream extraction systems.

Water Soluble Carbohydrates and Materials Removal

The exiting liquid from the aqueous separator is continuously transferred to a water soluble carbohydrates solution storage tank. It is anticipated that essentially all or any of the natural rubber latex rubber will attach to the chopped and milled biomass and will not be present in the liquid of this tank. If latex rubber is present in the liquid it will float to the top of the storage tank and be skimmed for collection, purification and sales of latex rubber solution or transferred to a coagulation tank where formic or another acid will be used to coagulate and solidify the natural rubber and then it will be continuously added with the water wet biomass feedstock into the solvent extraction system for natural organics and rubber recovery.

The dilute water soluble carbohydrates solution is transferred to a micron size of less than 100 microns, polishing type filter to remove the majority of the fine suspended solids primarily *Taraxacum* fine particle plant materials. The filtered dilute water soluble carbohydrates solution is continuously transferred at a controlled flow rate to a concentration system that removes the bulk of the water and produces moderate viscosity mixed carbohydrates syrup. The concentration system is preferred to be a multi stage steam heated evaporation system with or without the option to provide vacuum to control the liquid temperature and the quality of the carbohydrates syrup. Other unit operations involving distillation, thin film evaporation, and any other separation technology can be used in place or in combination thereof. The concentrated carbohydrates syrup solution is transferred to a final polishing filter to remove fine suspended solids formed during the concentration step to a micron size of less than 100 microns and then transferred to a purified and concentrated carbohydrates syrup storage tank. The storage tank is maintained with jacketed heating at a temperature to prevent crystallization and to control the viscosity for product transfer to packaging, bulk shipping via tank truck or rail car, or transfer to internal downstream processing like drying and or processing using the carbohydrates as feedstock for other chemical processes including synthesis and or fermentation processes to produce biofuels.

The evaporated water from the concentration system is condensed and collected and reused as recycle water for all of the manufacturing facility processing steps requiring water as feedstock. The harvested *Taraxacum* plant crowns and roots contain 75-85 weight percent water and will drastically reduce the resulting fresh water usage, consumption requirements, and expense cost for the entire facility. The process water recycle and recovery system will dramatically reduce the volume and expense costs for waste water disposal and its corresponding environmental impact from this facility. In addition, the facility can be economically viable when the facility is located in areas of the world located where water is scarce and available at higher than the typical costs in the United States of America.

Organic Polar Solvent Extraction Process

The water wet carbohydrate-depleted biomass solids from the aqueous process solid liquid separator are continuously transferred to a holding tank or silo for interim storage. If the facility would like to store the carbohydrate-depleted biomass solids in lieu of processing, a biomass dryer of any type operating at a maximum temperature of 100 C such that the targeted products are not thermally decomposed can be installed to remove 90+ weight percent of the water content of the carbohydrate-depleted biomass solids and the dried carbohydrate-depleted biomass solids can be hydraulically compacted and stored in a weather protected warehouse or storage area for processing at a later date. This option allows the facility to process all of the harvested *Taraxacum* for continuous water soluble carbohydrates production and hold and store compacted high density dried carbohydrate-depleted biomass solids for additional processing at a later date and operate the remaining solvent product and byproduct extractions in long continuous campaigns and when fresh harvested biomass is not available. This method offers flexibility and cost effective utilization of invested capital and manufacturing operating labor and expenses.

The first well agitated organic polar solvent extraction CSTE stage can be jacketed for steam heating with an overhead reflux condenser to minimize solvent losses. The organic polar solvent is chosen based on the solubility to dissolve the soluble natural organic compounds without dissolving the high molecular weight natural rubber and its ability to dehydrate and remove the remaining water in the water wet carbohydrate-depleted biomass solids. It is most desirable for the organic polar solvent to be low cost and readily available in the area of the processing facility. Acetone has been found to dissolve these organic chemicals found in the *Taraxacum* crown and root biomass in the range of 0.5 to 5 weight percent on a dry weight basis. Water is soluble in Acetone and therefore it is an excellent low cost solvent for water dehydration of the biomass. Water wet Acetone at approximately 98 wt. % with 2 wt. % water offers an economic cost savings vs. dry acetone for this process. Other organic polar solvents such as methanol, ethanol, propanol, isopropanol, butanol, iso-butanol, tertiary butyl alcohol, methyl ethyl ketone, methyl isobutyl ketone, furfuryl alcohol, tetrahydrofurfuryl alcohol, and any other organic polar solvents can be used as the polar solvent for this process. Combinations of polar solvents are also included but will increase the cost of capital and operating expense for solvent recovery and reuse and are not recommended without demonstrated requirements and justification. The temperature of the continuous organic polar solvent extraction can be operated at the boiling point of the chosen solvent at atmospheric pressure with the addition of a reflux condenser. The operating temperature can be increased above the boiling point with the use of CSTE stages comprising a pressure vessel or tank designed in accordance with the appropriate pressure vessel codes and requirements at the location of the facility.

The water wet biomass in interim storage is continuously transferred at a measured and controlled flow rate to the first well agitated organic polar solvent CSTE stage. Simultaneously, the organic polar solvent is continuously transferred at a measured and controlled flow rate to the first well agitated polar solvent CSTE stage. The objective of the organic polar solvent extraction process is to achieve a high removal and yield a minimum of 90 weight percent on a dry weight basis of the natural organics and water contained in the carbohydrate-depleted biomass solids feedstock. The organic polar solvent liquid slurry phase extraction can be accomplished to meet the objectives by utilizing co-current well stirred CSTE stages in series. The overall residence time, incubation time, and/or cycle for this continuous liquid organic polar solvent phase extraction is controlled by the flow rate of the feedstock and the organic polar solvent that is the biomass to solvent ratio, the volume of each CSTE stage in the system, and the number of well stirred and agitated CSTE stages in the CSTE system. The total anticipated residence time for this continuous organic polar solvent slurry phase extraction process is a minimum of 1 hour and a maximum of 8 hours. The contents of the last well stirred and agitated extraction stage is transferred to a solid liquid separator having the ability to handle flammable solvents. Continuous centrifuges of many types and configurations, as well as other continuous pressure filtration processes such as a Funda, Schenk, or similar filtering systems can be used in any configuration or combination as equipment to complete this process. The polar compound-depleted biomass solids can be washed with clean recycled or fresh organic polar solvent to remove residual polar organic compounds from the exiting polar compound-depleted biomass solids for yield improvement. The separated liquid polar organics fraction that contains useful polar organic compounds can be subjected to further processing for final product recovery and purification.

The organic polar solvent liquid extraction can also be done in a continuous countercurrent liquid extraction system manufactured by Crown Iron Works-USA, Desmet Ballestra-Belgium, Sliding Cell Extractor or "Lurgi" devices (Air Liquide Engineering and Construction, Paris, France), and any other continuous liquid solid phase solvent extraction machine or system where the extraction process variables are controlled. When using the Crown Iron Works or similar extraction system, the polar compound-depleted biomass solids exit the system without the need of a centrifuge or any other solid-liquid separator.

Polar Organics Fraction Processing

The polar organics fraction is continuously transferred from the solid liquid separator for the continuous slurry phase extraction system or the Crown Iron Works or equivalent continuous extraction system to a polar organics fraction storage tank. The polar organics fraction is continuously transferred to a micron size of less than 100 microns, polishing type filter to remove the majority of the suspended solids primarily *Taraxacum* fine particle plant materials. The filtered dilute polar organics fraction contains natural *Taraxacum* organic chemicals that can be temperature sensitive and the solution is then separated by thermally controlled distillation and/or evaporation to remove both the water and the remaining organic polar solvent. This is done in the continuous polar organics fraction stripper or evaporation system and can be followed by a continuous thin film evaporator to remove the remaining polar solvent at thermally controlled conditions. The hot concentrated polar organics fraction finished product and/or by-products are transferred to a finished product concentrated polar organics fraction or by-product storage tank The concentrated polar organics fraction can be further processed to recover and purify individual products. The finished concentrated polar organics fraction product or products are transferred to either a packaging area or a bulk loading area for sales.

The finished concentrated polar organics fraction products can contain polar organic compounds that are unique in composition and quantity to the *Taraxacum* plant. These chemicals have market value as lubricants, cosmetic ingredients, insect pheromones, sealants, adhesives, surfactants, or emulsifiers.

The organic polar solvent and water removed in the stripper is continuously transferred to a dehydrator to remove the water producing a cleaned organic polar solvent that is stored for reuse and recycle for the organic polar solvent extraction process. The dehydrator is preferred to be a water adsorption system using molecular sieves as the adsorption medium. The dehydration can also be accomplished using specialized pressure swing type distillation to break any azeotropes formed with water when dry polar solvent is required.

Organic Non-Polar Solvent Extraction Process

The wet or, if desired dried, polar compound-depleted biomass solids from the continuous polar solvent slurry phase extraction solid liquid separator or from the polar solvent CSTE system is continuously transferred to a first well agitated non polar solvent CSTE stage. The first well agitated non polar solvent CSTE stage can be jacketed for steam heating with an overhead reflux condenser to minimize solvent losses when operated at atmospheric pressure. The non-polar organic solvent is chosen based on the solubility to dissolve the natural high molecular weight *Taraxacum* rubber without dissolving, or with only minimized dissolving, of other organics that can contaminate the quality of the natural rubber product. In certain processes, the polar solvent remaining in the feedstock polar compound-depleted biomass solids is soluble in the non-polar organic solvent and will not interfere with the extraction of natural rubber in the organic non polar solvent. It is most desirable for the organic non polar solvent to be low cost and readily available in the area of the processing facility. Mixed Hexanes has been found to dissolve the natural rubber in the *Taraxacum* crown and root biomass in the range of 0.5 to 25 weight percent on a dry weight basis. Other organic non polar solvents such as n-hexane, cyclohexane, pentane, tetrahydrafuran, toluene, and any other non-polar organic solvents can be used as the non-polar organic solvent for this process. Combinations of polar solvents are also included but will increase the cost of capital and operating expense for solvent recovery and reuse and are not recommended without demonstrated requirements and justification. The temperature of the continuous solvent extraction can be operated at the boiling point of the chosen solvent at atmospheric pressure with the addition of a reflux condenser. The operating temperature can be increased above the boiling point with the use of pressure vessels designed in accordance with the appropriate pressure vessel codes and requirements at the location of the facility.

The polar compound-depleted biomass solids in interim storage can be continuously transferred at a controlled flow rate to the first well agitated non-polar organic solvent CSTE stage. Simultaneously, the non-polar organic solvent is continuously transferred at a controlled flow rate to the first well agitated non polar solvent CSTE stage. In certain cases, the objective of the non-polar organic solvent extraction process is to achieve a removal and yield a minimum of 90 weight percent on a dry weight basis of the natural rubber contained in the biomass feedstock. The non-polar organic solvent liquid slurry phase extraction can be accomplished to meet the objectives by utilizing co-current well stirred CSTE stages in series. The overall residence, cycle, and/or incubation time for this continuous liquid solvent phase extraction is controlled by the flow rate of the feedstock and the non-polar organic solvent that is the solvent to biomass ratio, the volume of each CSTE stage in the system, and the number of well stirred and agitated CSTE stage in the system. The total anticipated residence time for this continuous non polar solvent slurry phase extraction process is a minimum of 1 hour and a maximum of 8 hours. The contents of the last well stirred and agitated CSTE stage is transferred to a solid liquid separator having the ability to handle flammable solvents. Continuous centrifuges of many types and configurations, as well as other continuous pressure filtration processes such as a Fundi, Schenk, or similar filtering systems can be used in any configuration or combination as equipment to complete this process. The spent biomass solids can be washed with fresh non polar solvent to remove residual natural rubber from the exiting biomass for yield improvement.

The non-polar organic solvent extraction can also be done in a continuous countercurrent liquid solid extraction system manufactured by Crown Iron Works-USA, Desmet Ballestra-Belgium, Sliding Cell Extractor or "Lurgi" devices (Air Liquide Engineering and Construction, Paris, France), and any other continuous liquid solid phase solvent extraction machine or system where the extraction process variables are controlled. When using the Crown Iron Works or similar extraction system, the non-polar organic solvent wet spent biomass exits the system without the need of a centrifuge or any other solid liquid separator. The rubber-containing non-polar solvent fraction liquid is also obtained from the solid liquid separator.

Rubber-Containing Non-Polar Solvent Fraction Processing

The rubber-containing non-polar solvent fraction is continuously transferred from the solid liquid separator for the continuous slurry phase extraction system or the Crown Iron Works or CSTE system to a rubber-containing non-polar solvent fraction storage tank. The rubber-containing non-polar solvent fraction is continuously transferred to a micron size of less than 100 microns, polishing type filter to remove the majority of the suspended solids primarily *Taraxacum* fine particle plant materials. The filtered dilute rubber-containing non-polar solvent fraction contains high molecular weight natural *Taraxacum* rubber that can be temperature sensitive and the solution is then volume reduced by thermally and or vacuum controlled distillation or evaporation to remove the major part of the non-polar organic solvent while maintaining the natural rubber in solution. This is done in the continuous rubber-containing non-polar solvent fraction stripper or evaporator. The temperature is controlled below 100. degrees. C. to avoid thermal decomposition of the high molecular weight rubber.

After the non-polar organic solvent has been reduced in volume to obtain a concentrated rubber-containing non-polar solvent fraction, a small amount of rubber antioxidant is added to the solution in line with an inline mixer and the solution is continuously transferred to the rubber precipitator tank at a measured and controlled flow rate. The antioxidant can be Santoflex 134PD (Eastman Chemicals, Kingsport, Tenn., USA) however other rubber antioxidants and potential product improvement additives can be added based on customer requirements for the finished product. The rubber precipitator tank is both agitated for mixing and jacketed for cooling and designed for easy removal of the precipitated rubber and the mixed liquid organic solvent mixture. An equal volume of the organic polar solvent is pre-cooled to a temperature of between 0 and 10.degrees.C and added continuously to the rubber precipitator tank with the concentrated rubber-containing non-polar solvent fraction with antioxidants. This will precipitate the natural rubber into a gelatinous solid that sinks to the bottom of the tank due to the density being greater than the density of the mixed solvent solution and leaves the organic impurities left in solution with the organic polar and non-polar organic solvent mixture (i.e., mixed liquid organic solvents) creating a high purity, high molecular weight anti-oxidized natural rubber product. The liquid mixture of organic polar and non-polar organic solvents is transferred to a mixed liquid organic solvent storage tank for inventory, recovery and reuse of the solvents.

The precipitated natural rubber product can be continuously removed from the precipitation tank and transferred to system(s) that remove mixed liquid organic solvents and form and/or shape the gelatinous precipitated rubber into uniform pieces of solid rubber and/or dried solid rubber. Mixed liquid organic solvents can be transferred to a mixed liquid organic solvent storage tank. The uniform pieces of solidified rubber are appropriately sized for optimum packaging, storage and shipment for customer sales and use. The uniform pieces of solidified rubber can be in the shape of sheets, square or rectangular blocks, cylindricals, or any shape or combination thereof. The mixed liquid organic solvent wet rubber pieces are continuously transferred to the temperature controlled solid rubber dryer where the balance of the mixed solvent is removed to produce a finished dried product of natural *Taraxacum* rubber. The condensed solvent mixture from the drying process is transferred to the mixed liquid organic solvent storage tank. The dry rubber pieces can be continuously transferred to a packaging system that loads the dried rubber pieces onto a standard pallet and the entire contents are sealed to minimize and prevent oxidation of the natural rubber and moved into storage and inventory to ship and transport the solid rubber product for customer sales. The solid natural rubber product can be used to manufacture a variety of goods that include, but are not limited to, tires.

The organic polar and non-polar organic solvent liquid mixture removed in the precipitator, by the systems that remove mixed liquid organic solvent and form and/or shape the gelatinous precipitated rubber, and/or by the dryer can be collected and stored in the liquid phase in the mixed liquid organic solvent storage tank. The mixed liquid organic solvent is continuously transferred to a distillation mixed solvent separation system. The separation system produces a cleaned polar solvent that is stored for reuse and recycle as feedstock for the polar solvent extraction process and a cleaned non polar solvent that is stored for reuse and recycled as feedstock for the non-polar organic solvent extraction process.

Spent Biomass Processing

Spent biomass from the continuous non polar solvent slurry phase extraction separator or from the Crown Iron Works or equivalent continuous solvent extraction system is continuously transferred to the spent biomass dryer. The spent biomass dryer evaporates and removes the non-polar organic solvent from the spent biomass and achieving a level below 1000 PPM. The evaporated solvent is condensed and transferred to storage for reuse and recycled as feedstock for the non-polar organic solvent extraction process.

Energy in the form of low pressure steam is required for many of the processes for this facility. Therefore, a steam boiler is required to supply the steam requirements for this continuous process. The dried spent biomass has a BTU content of approximately 7,500 BTU per pound and can be used as feedstock for the boiler. The boiler will be equipped to use either natural gas, fuel oil, or any other readily available and low cost fuel to supplement the energy requirements of the facility.

The breadth and scope of the present disclosure should not be limited by any of the above-described examples, but should be defined only in accordance with the following embodiments, the following claims, and their equivalents.

EMBODIMENTS

Embodiment 1

A processing system for obtaining a carbohydrate-containing liquid and a carbohydrate-depleted biomass solids from a rubber bearing plant comprising: an extraction system comprising a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, at least one of the continuous stirred tank extraction stages in each extraction system having an inlet adapted and configured to receive a liquid solvent, wherein the at least one continuous stirred extraction stage of the extraction system is adapted and configured for receiving biomass and a liquid solvent comprising water, an aqueous solution, or a combination thereof at a temperature of at least about 50° C., wherein the biomass is from a rubber bearing plant of the genus *Taraxacum* or another non-*Hevea* plant, and wherein the extraction system is adapted and configured to mix the biomass with the liquid solvent in a manner such that the extraction system generates the carbohydrate-containing liquid and the carbohydrate-depleted biomass solids; and a solid-liquid separator arranged in fluid communication with a last in series of the continuous stirred tank extraction stages, wherein the separator is adapted and configured for separating the carbohydrate-depleted biomass solids from the carbohydrate-containing liquid.

Embodiment 2

A processing system for obtaining a polar organics fraction and polar compound-depleted biomass solids from a rubber bearing plant comprising: an extraction system comprising a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, at least one of the continuous stirred tank extraction stages in each extraction system having an inlet adapted and configured to receive a liquid organic solvent, wherein the at least one continuous stirred extraction stage of the extraction system is adapted and configured for receiving carbohydrate-depleted biomass solids and an organic polar solvent liquid, wherein the carbohydrate-depleted biomass solids are from a rubber bearing plant of the genus *Taraxacum* or another non-*Hevea* plant, and wherein the extraction system is adapted and configured to mix the carbohydrate-depleted biomass solids with the organic polar solvent in a manner such that the extraction system generates the liquid polar organics fraction and the polar compound-depleted biomass solids; and a solid-liquid separator arranged in fluid communication with a last in series of the continuous stirred tank extraction stages, wherein the separator is adapted and configured for separating the polar compound-depleted biomass solids from the liquid polar organics fraction.

Embodiment 3

A processing system for obtaining a rubber-containing non-polar solvent fraction and spent biomass solids from a rubber bearing plant comprising: an extraction system comprising a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, at least one of the continuous stirred tank extraction stages in each extraction system having an inlet adapted and configured to receive a liquid solvent, wherein the at least one continuous stirred extraction stage of the extraction system is adapted and configured for receiving polar compound-depleted biomass solids and a non-polar organic solvent, wherein the polar compound-depleted biomass solids are from a rubber bearing plant of the genus *Taraxacum* or another non-*Hevea* plant, and wherein the extraction system is adapted and configured to mix the polar compound-depleted biomass solids with the non-polar organic solvent in a manner such that the extraction system generates the rubber-containing non-polar solvent fraction liquid and the spent biomass solids; and a solid-liquid separator arranged in fluid communication with a last in series of the continuous stirred tank extraction stages, wherein the separator is adapted and configured for separating the spent biomass solids from the rubber-containing non-polar solvent fraction liquid.

Embodiment 4

A processing system for obtaining a rubber containing fraction from a rubber bearing plant comprising: (a) a first extraction system adapted and configured: to receive biomass from the plant or parts thereof and a liquid solvent comprising water, an aqueous solution, or a combination thereof, to mix the biomass and liquid solvent at a temperature of at least about 50° C. in a manner such that the first extraction system generates a carbohydrate-containing liquid and a carbohydrate-depleted biomass solids; and to separate the carbohydrate-depleted biomass solids from the carbohydrate-containing liquid; wherein the rubber bearing plant is of the genus *Taraxacum* or is another non-*Hevea* plant; (b) a second extraction system adapted and configured: to receive the carbohydrate-depleted biomass solids from the first extraction system; to mix the carbohydrate-depleted biomass solids with an organic polar solvent in a manner such that the second extraction system generates a liquid polar organics fraction and polar compound-depleted biomass solids; and to separate the liquid polar organics fraction and polar compound-depleted biomass solids; and (c) a third extraction system adapted and configured to: receive the polar compound-depleted biomass solids from the second extraction system and a non-polar organic solvent; to mix the polar compound-depleted biomass solids with the non-polar organic solvent in a manner such that the third extraction system generates a rubber-containing non-polar solvent fraction liquid and spent biomass solids; and to separate the rubber-containing non-polar solvent fraction liquid and spent biomass solids; wherein at least one of the first, second, or third extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, and each extraction system further comprising a solid-liquid separator arranged in fluid communication with a last in series of the continuous stirred tank extraction stages of the respective extraction system, wherein the solid-liquid separator is adapted and configured to separate the carbohydrate-depleted biomass solids, polar compound-depleted biomass solids, or spent biomass solids from the carbohydrate-containing liquid, the liquid polar organics fraction, or the rubber-containing non-polar solvent fraction liquid.

Embodiment 5

The processing system of embodiment 4, wherein one or two of the extraction systems comprise a Soxhlet extractor, an immersion extractor, a counter current immersion extractor, or a percolation extractor.

Embodiment 6

A processing system for obtaining a rubber containing fraction from a rubber bearing plant comprising: (a) a first extraction system adapted and configured: to receive biomass from the plant or parts thereof and an organic polar solvent; to mix the biomass with an organic polar solvent in a manner such that the second extraction system generates a liquid polar organics fraction and polar compound-depleted biomass solids; and to separate the liquid polar organics fraction and polar compound-depleted biomass solids; and (c) a second extraction system adapted and configured to: receive the polar compound-depleted biomass solids from the first extraction system; to mix the polar compound-depleted biomass solids with a non-polar organic solvent in a manner such that the second extraction system generates a rubber-containing non-polar solvent fraction and spent biomass solids; and to separate the rubber-containing non-polar solvent fraction and spent biomass solids; wherein at least one of the first or second extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, and each extraction system further comprising a solid-liquid separator arranged in fluid communication with a last in series of the continuous stirred tank extraction stages of the respective extraction system, wherein the solid-liquid separator is adapted and configured to separate the polar compound-depleted biomass solids or spent biomass solids from the liquid polar organics fraction or the rubber-containing non-polar solvent fraction.

Embodiment 7

The processing system of embodiment 6, wherein one of the extraction systems comprise a Soxhlet extractor, an immersion extractor, a counter current immersion extractor, or a percolation extractor.

Embodiment 8

The processing system of any one of embodiments 1-7, further comprising a solids conditioning and preparation machine(s) adapted and configured to reduce particle size, and/or alter the shape and condition of the solid material prior to introduction of the solid material into at least one continuous stirred tank extraction stage.

Embodiment 9

The processing system of any one of embodiments 1-7, further comprising a recirculation loop associated with the at least one continuous stirred tank extraction stage.

Embodiment 10

The processing system of embodiment 9, wherein the recirculation loop includes a heat exchanger or heat transfer device.

Embodiment 11

The processing system of embodiment 9, wherein the recirculation loop includes a particle reduction and/or shape altering device.

Embodiment 12

The processing system of any one of embodiments 1-11, wherein the at least one continuous stirred tank extraction stage has blades adapted and configured to increase shear to reduce and/or alter the particle size and shape of the biomass, carbohydrate-depleted biomass solids, polar compound depleted biomass solids, or spent biomass solids.

Embodiment 13

The processing system of any one of embodiments 1, 4, or 5, wherein at least one CSTE stage is adapted and configured to receive and contain the liquid solvent at a temperature of about 50° C. to about 100° C.

Embodiment 14

The processing system of any one of embodiments 1, 4, or 5, wherein at least one CSTE stage is adapted and configured to receive and contain the liquid solvent at a temperature of above 100° C. and at a pressure that is greater than atmospheric pressure.

Embodiment 15

A method for extracting carbohydrate-containing liquid from a rubber bearing plant, the method comprising: introducing a liquid solvent comprising water, an aqueous solution, or a combination thereof and biomass from the plant or a part thereof into at least one continuous stirred tank extraction stage of a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, wherein the rubber bearing plant is of the genus *Taraxacum* or is another non-*Hevea* plant; introducing into the at least one continuous stirred tank extraction stage a liquid solvent comprising water, an aqueous solution, or a combination thereof and the biomass; mixing the liquid solvent with the biomass in the at least one continuous stirred tank extraction stage at a temperature of at least about 50° C. to enable the carbohydrates associated with the biomass to be extracted in the liquid solvent; and introducing an effluent from the at least one continuous stirred tank extraction stage into a solid-liquid separator to result in a separated carbohydrate-containing liquid and a carbohydrate-depleted biomass solids.

Embodiment 16

A method for extracting a polar organics fraction from carbohydrate-depleted biomass solids of a rubber bearing plant, the method comprising: introducing an organic polar solvent and the carbohydrate-depleted biomass solids into at least one continuous stirred tank extraction stage of a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, wherein the rubber bearing plant is of the genus *Taraxacum* or is another non-*Hevea* plant; mixing the organic polar solvent with the carbohydrate-depleted biomass solids in the at least one continuous stirred tank extraction stage in a manner to enable the polar organics fraction associated with the solid to be extracted in the organic polar solvent; and introducing an effluent from the at least one continuous stirred tank extraction stage into a solid-liquid separator to result in a separated polar organics fraction liquid and polar compound-depleted biomass solids.

Embodiment 17

A method for extracting a rubber-containing non-polar solvent fraction from polar compound-depleted biomass solids of a rubber bearing plant, the method comprising: introducing a non-polar organic solvent and polar compound-depleted biomass solids into at least one continuous stirred tank extraction stage of a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages, wherein the rubber bearing plant is of the genus *Taraxacum* or is another non-*Hevea* plant; mixing the non-polar organic solvent with the polar compound-depleted biomass solids in the at least one continuous stirred tank extraction stage in a manner to enable the natural rubber associated with the solid to be extracted in the non-polar organic solvent; and introducing an effluent from the at least one continuous stirred tank extraction stage into a solid-liquid separator to result in a separated rubber-containing non-polar solvent fraction and spent biomass solids.

Embodiment 18

A method for extracting a rubber-containing non-polar solvent fraction from a rubber bearing plant, the method comprising (a) introducing into a first extraction system biomass from the plant or parts thereof and a liquid solvent comprising water, an aqueous solution, or a combination thereof; mixing the biomass and liquid solvent at a temperature of at least about 50° C. to generate a carbohydrate-containing liquid and a carbohydrate-depleted biomass solids; and separating the carbohydrate-depleted biomass solids from the carbohydrate-containing liquid; wherein the rubber bearing plant is of the genus *Taraxacum* or is another non-*Hevea* plant; (b) introducing into a second extraction system the carbohydrate-depleted biomass solids from the first extraction system an organic polar solvent; mixing the carbohydrate-depleted biomass solids with the organic polar solvent to generate a liquid polar organics fraction and polar compound-depleted biomass solids, and separating the liquid polar organics fraction and polar compound-depleted biomass solids; and, (c) introducing into a third extraction system the polar compound-depleted biomass solids from the second extraction system and a non-polar organic solvent; mixing the polar compound-depleted biomass solids with the non-polar organic solvent to generate a rubber-containing non-polar solvent fraction and spent biomass solids; and separating the rubber-containing non-polar solvent fraction and spent biomass solids; wherein at least one of the first, second, or third extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, and each extraction system further comprising a solid-liquid separator arranged in fluid communication with a last in series of the continuous stirred tank extraction stages of the respective extraction system, wherein the solid-liquid separator is adapted and configured to separate the carbohydrate-depleted biomass solids, polar compound-depleted biomass solids, or spent biomass solids from the carbohydrate-containing liquid, the liquid polar organics fraction, or the rubber-containing non-polar solvent fraction.

Embodiment 19

The method of embodiment 14, wherein one or two of the extraction systems comprise a Soxhlet extractor, an immersion extractor, a counter current immersion extractor, or a percolation extractor.

Embodiment 20

A method for extracting a rubber-containing non-polar solvent fraction from a rubber bearing plant, the method comprising (a) introducing into a first extraction system biomass from the plant or parts thereof and an organic polar solvent; mixing the biomass with the organic polar solvent to generate a liquid polar organics fraction and polar compound-depleted biomass solids, and separating the liquid polar organics fraction and polar compound-depleted biomass solids; wherein the rubber bearing plant is of the genus *Taraxacum* or is another non-*Hevea* plant; (b) introducing into a second extraction system the polar compound-depleted biomass solids from the first extraction system and a non-polar organic solvent; mixing the polar compound-depleted biomass solids with the non-polar organic solvent to generate a rubber-containing non-polar solvent fraction and spent biomass solids; and separating the rubber-containing non-polar solvent fraction and spent biomass solids; wherein at least one of the first or second extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, and each extraction system further comprising a solid-liquid separator arranged in fluid communication with a last in series of the continuous stirred tank extraction stages of the respective extraction system, wherein the solid-liquid separator is adapted and configured to separate the polar compound-depleted biomass solids, or spent biomass solids from the liquid polar organics fraction or the rubber-containing non-polar solvent fraction.

Embodiment 21

The method of any one of embodiments 15, 16, 17, 18, 19, or 20, wherein parts of the plant comprising shoots, flowers, leaves, roots, crowns, or a combination thereof are used as biomass feedstock.

Embodiment 22

The method of embodiment 21, wherein the plant is of the genus *Taraxacum* and wherein parts of the plant comprise roots, crowns, or a combination thereof.

Embodiment 23

The method of embodiment 22, wherein the plant of the genus *Taraxacum* is *T. koksaghyz* or a cultivar thereof, a variety comprising introgressed germplasm from one or more *Taraxacum* species or cultivars, a variety comprising inter-specific hybrid germplasm, a variety comprising hybrid germplasm from two or more cultivars, a variety arising from mutagenesis or gene-editing of any rubber bearing *Taraxacum* species, cultivars, or variety, a transgenic *Taraxacum* plant, or any combination thereof.

Embodiment 24

The method of embodiment 23, wherein the variety comprises inter-specific hybrid germplasm of *T. koksaghyz* and *T. officinale*.

Embodiment 25

The method of embodiment 24, wherein the biomass used as feedstock in the method is obtained from one or more than one of the plants, varieties, or cultivars.

Embodiment 26

The method of embodiment 15, 18, or 19, wherein the pH of the water, aqueous solution, or combination thereof has a value of greater than 7 but less than or equal to about 10.

Embodiment 27

The method of any one of embodiments 15, 18, or 19, wherein the liquid solvent is at a temperature of about 50° C. to about 100° C.

Embodiment 28

The method of any one of embodiments 15, 18, or 19, wherein the liquid solvent is at a temperature of above 100° C. and at a pressure that is greater than atmospheric pressure.

Embodiment 29

The method of any one of embodiments 15, 18, or 19, wherein the carbohydrates are used as feedstock in a chemical or fermentation process.

Embodiment 30

The method of any one of embodiments 15, 18, or 19, further comprising drying the carbohydrate-depleted biomass solids or a portion thereof.

Embodiment 31

The method of embodiment 16, 18, 19, 20, or 21, wherein the organic polar solvent comprises an alcohol having 1 to 8 carbon atoms, a ketone having 3 to 8 carbon atoms, a hydroxy ketone having 3 to 8 carbon atoms, a ketol, an ester having 3 to 8 carbon atoms, or a combination thereof.

Embodiment 32

The method of embodiment 31, wherein the organic polar solvent comprises acetone, methanol, ethanol, propanol, isopropanol, butanol, iso-butanol, tertiary butyl alcohol, methyl ethyl ketone, methyl isobutyl ketone, furfuryl alcohol, tetrahydrofurfuryl alcohol, a water-wet form thereof

Embodiment 33

The method of any one of embodiments 15-31 or 32, further comprising recirculating effluent associated with the at least one continuous stirred tank extraction stage and reducing a particle size and/or altering particle shape and/or shearing to expose the fibers of the solid material in the effluent during recirculating of the effluent.

Embodiment 34

The method of embodiment 33 further comprising recirculating effluent associated with the at least one continuous stirred tank extraction stage and altering the pressure and temperature of the effluent to increase a solubility of the product(s) in the solvent.

Embodiment 35

The method of any one of embodiments 15-33, or 34, wherein the step of mixing the biomass, carbohydrate-depleted biomass solids, or polar compound-depleted biomass solids with the liquid solvent-or solvent includes reducing and or shearing the particle size of and shape of the biomass, carbohydrate-depleted biomass solids, or polar compound-depleted biomass solid in the at least one continuous stirred tank extraction stage.

Embodiment 36

The method of any one of embodiments 16, 18, 19, or 22-35 wherein the carbohydrate-depleted biomass solids are extracted with the organic polar solvent for about 1 to about 8 hours.

Embodiment 37

The method of 16, 18, 19, or 22-36 further comprising the step of filtering the polar organics fraction to separate fine solid particles after the solid-liquid separation.

Embodiment 38

The method of embodiment 16, 18, 19, or 22-37, further comprising the step of obtaining a polar organic sub-fraction enriched for a lubricant, a cosmetic ingredient, an insect pheromone, a sealant, an adhesive, a surfactant, or an emulsifier from the polar organics fraction.

Embodiment 39

The method of embodiment 38 wherein the polar organic sub-fraction is enriched for at least one of 18-oxo-nonadecanoic acid, palmitic acid ethyl ester, oleanolic acid, cholecalciferol, 17-hydroxy-9Z-octadecenoic acid, sphingosine, 12-oxo-9-octadecynoic acid, cis-5-tetradecenoylcarnitine, azelaic acid, monoolein, beta-hydroxypalmitic acid, dodecylbenzenesulfonic acid, cis-9-hexadecenoic acid, or an isomer thereof

Embodiment 40

The method of any one of embodiments 17-38 wherein the non-polar organic solvent comprises a hydrocarbon having 1 to 16 carbon atoms.

Embodiment 41

The method of embodiment 40, wherein the hydrocarbon is selected from the group consisting of alkanes having 4 to 9 carbon atoms, cycloalkanes and having 5 to 10 carbon atoms, alkyl substituted cycloalkanes having 5 to 10 carbon atoms, aromatic compounds having 6 to 12 carbon atoms, and alkyl substituted aromatic compounds having 7 to 12 carbon atoms.

Embodiment 42

The method of embodiment 40, wherein the non-polar organic solvent comprises n-hexane, mixed hexanes, cyclohexane, n-pentane, mixed pentanes, 2-methylpentane, 3-methylpentane, 2,3-dimethylbutane, 2-2-dimethylbutane, methylcyclopentane, toluene, xylene, tetrahydrafuran, or a mixture thereof.

Embodiment 43

The method of any one of embodiments 17-42, wherein the polar compound-depleted biomass solids are extracted with the non-polar organic solvent for about 1 hour to about 8 hours.

Embodiment 44

The method of any one of embodiments 17-43, wherein the polar compound-depleted biomass solids are extracted with the non-polar organic solvent at atmospheric pressure and at a temperature below or at the boiling point of the non-polar organic solvent at atmospheric pressure.

Embodiment 45

The method of any one of embodiments 17-43, wherein the polar compound-depleted biomass solids are extracted with the organic non-polar solvent at a temperature above the boiling point of the non-polar organic solvent at atmospheric pressure and at a pressure that is above atmospheric pressure.

Embodiment 46

The method of any one of embodiments 17-45, wherein the separation of the rubber-containing non-polar solvent fraction from the spent biomass solids is effected by centrifugation, filtration, settling, dissolved gas flotation or a combination thereof.

Embodiment 47

The method of any one of embodiments 17-45, wherein at least 80%, 90%, 95%, 98%, or 99% by dry weight of the natural rubber contained in a biomass or polar compound-depleted biomass solids feedstock is extracted in the rubber-containing non-polar solvent fraction.

Embodiment 48

The method of embodiment 17-46 or 47, further comprising at least one of the following steps of: (a) filtering the rubber-containing non-polar solvent fraction; (b) distilling or evaporating at least half of the non-polar organic solvent while maintaining the rubber in solution to obtain a concentrated rubber solution; (c) adding an anti-oxidant to a concentrated rubber solution; (d) adding a cooled organic polar solvent to the concentrated rubber solution of (b) or (c) to precipitate the natural rubber; (e) further cooling the mixture of the organic polar solvent and non-polar organic solvent and precipitated rubber to form a gelatinous rubber precipitate and a mixed liquid organic solvent. (f) separating and removing the gelatinous rubber precipitate from the mixed liquid organic solvent; (g) forming and/or shaping the gelatinous rubber precipitate and/or further removing a portion of the mixed liquid organic solvent; (h) drying the formed and/or shaped gelatinous rubber precipitate to obtain a dried solid rubber product; (i) any combination of steps (a)-(h).

Embodiment 49

The method of embodiment 48, wherein the plant is of the genus *Taraxacum*, wherein the biomass is obtained from parts of the *Taraxacum* plant comprising leaves, stems, flowers, roots, crowns, or a combination thereof, and wherein the rubber-containing non-polar solvent fraction, gelatinous rubber precipitate, or dried solid rubber comprises polyisoprene having at least one of: (i) a unimodal molecular weight distribution with a Polydispersity (P) of 1.1 to 4 and a weight-average molecular weight of about $1.0 \times 10^6$ to $5.0 \times 10^6$ grams per mole, wherein the Polydispersity and the weight-average molecular weight are determined by an analytical method selected from the group consisting of Gel Permeation Chromatography (GPC) in combination with Evaporative Light Scattering Detection (GPC-ELSD), GPC in combination with multi-angle light scattering (GPC-MALS), and GPC in combination with Refractive Index (GPC-RI); (ii) an ash content of less than 0.5%, 0.4%, 0.3%, 0.2%, or 0.1%, by weight; and/or (iii) a nitrogen content of less than 0.5%, 0.4%, 0.3%, 0.2%, or 0.1% by weight.

Embodiment 50

The method of embodiment 48, wherein the plant is of the genus *Taraxacum*, wherein the biomass is obtained from parts of the *Taraxacum* plant comprising leaves, stems, flowers, roots, crowns, or a combination thereof, and wherein the rubber-containing non-polar solvent fraction, gelatinous rubber precipitate, or dried solid rubber has an ash content of less than 0.5%, 0.4, 0.3, 0.2%, or 0.1% by weight and a nitrogen content of less than 0.5, 0.4%, 0.3%, 0.2%, or 0.1%, % by weight.

Embodiment 51

The method of embodiment 48, wherein the plant is of the genus *Taraxacum*, wherein the biomass is obtained from parts of the *Taraxacum* plant comprising roots, crowns, or a combination thereof, and wherein polyisoprene in the rubber containing fraction, gelatinous rubber precipitate, or dried solid rubber has an essentially unimodal molecular weight distribution with a Polydispersity (P) of 1 to 4 and a weight-average molecular weight of about $1.0 \times 10^6$ to $5.0 \times 10^6$ grams per mole, wherein the Polydispersity and the weight-average molecular weight are determined by an analytical method selected from the group consisting of (GPC) in combination with Evaporative Light Scattering Detection (GPC-ELSD), GPC in combination with Multi-Angle Light scattering (GPC-MALS), and GPC in combination with Refractive Index (GPC-RI).

Embodiment 52

The method of embodiment 48, wherein the rubber-containing non-polar solvent fraction, gelatinous rubber precipitate, or dried solid rubber have an ash content of less than 0.5%, 0.4%, 0.3%, 0.2%, or 0.1% by weight.

Embodiment 53

The method of embodiment 48, wherein the plant is of the genus *Taraxacum*, wherein the biomass is obtained from parts of the *Taraxacum* plant comprising leaves, stems, flowers, roots, crowns, or a combination thereof, and wherein the rubber-containing non-polar solvent fraction, gelatinous rubber precipitate, or dried solid rubber have a nitrogen content of less than 0.5% by weight.

Embodiment 54

The method of any one of embodiments 15-53 or 54, wherein the method is continuous.

Embodiment 55

The method of any one of embodiments 15-53 or 54, wherein the method is semi-continuous or batch mode.

Embodiment 56

The method of any one of embodiments 17-54 or 55, wherein the spent biomass is dried with a liquid content at or below 0.1 weight percent.

Embodiment 57

The method of embodiment 56, wherein the dried spent biomass is used as a feedstock for a boiler, feedstock for biofuel production, an animal feed supplement, cellulose insulation, additive or filler for particle board, soil improvement, building supplies, or any combination thereof.

Embodiment 58

The processing system of any one of embodiments 1-14, wherein at least a first and any subsequent CSTE stage of the CSTE stages in at least one extraction system have: (i) an inlet adapted and configured to receive the liquid solvent; (ii) an inlet adapted and configured to receive the biomass, the carbohydrate-depleted biomass solids, or the polar compound-depleted biomass solids; or (iii) a combination of an inlet of (i) and an inlet of (ii).

Embodiment 59

The processing system of embodiment 58, wherein each CSTE stage of the CSTE stages in at least one extraction system have: (i) an inlet adapted and configured to receive the liquid solvent; (ii) an inlet adapted and configured to receive the biomass, the carbohydrate-depleted biomass solids, or the polar compound-depleted biomass solids; or (iii) a combination of an inlet of (i) and an inlet of (ii).

Embodiment 60

The method of any one of embodiments 15-56, or 57 wherein at least a first and any subsequent CSTE stage of the CSTE stages in at least one extraction system have: (i) inlet adapted and configured to receive the liquid solvent; (ii) an inlet adapted and configured to receive the biomass, the carbohydrate-depleted biomass solids, or the polar compound-depleted biomass solids; or (iii) a combination of an inlet of (i) and an inlet of (ii).

Embodiment 61

The method of embodiment 60, wherein each CSTE stage of the CSTE stages in at least one extraction system have: (i) inlet adapted and configured to receive the liquid solvent; (ii) an inlet adapted and configured to receive the biomass, the carbohydrate-depleted biomass solids, or the polar compound-depleted biomass solids; or (iii) a combination of an inlet of (i) and an inlet of (ii). cm What is claimed is:

What is claimed is:

1. A processing system for obtaining a rubber containing fraction from a rubber bearing plant comprising:
   (a) a first extraction system adapted and configured: to receive biomass from the plant or parts thereof and a liquid solvent comprising water, an aqueous solution, or a combination thereof; to mix the biomass and liquid solvent at a temperature of at least about 50° C. in a manner such that the first extraction system generates a carbohydrate-containing liquid and a carbohydrate-depleted biomass solids; and to separate the carbohydrate-depleted biomass solids from the carbohydrate-containing liquid; wherein the rubber bearing plant is of the genus *Taraxacum* or is another non-*Hevea* plant;
   (b) a second extraction system adapted and configured: to receive the carbohydrate-depleted biomass solids from the first extraction system and an organic polar solvent; to mix the carbohydrate-depleted biomass solids with the organic polar solvent in a manner such that the second extraction system generates a liquid polar organics fraction and polar compound-depleted biomass solids; and to separate the liquid polar organics fraction and polar compound-depleted biomass solids; and
   (c) a third extraction system adapted and configured to: receive the polar compound-depleted biomass solids from the second extraction system and a non-polar organic solvent; to mix the polar compound-depleted biomass solids with the non-polar organic solvent in a manner such that the third extraction system generates a rubber-containing non-polar solvent fraction and spent biomass solids; and to separate the rubber-containing non-polar solvent fraction and spent biomass solids;
   wherein at least one of the first, second, or third extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, the at least one continuous stirred tank extraction stage is adapted and configured to mix and form a homogeneous slurry, the homogeneous slurry corresponding to the solvent and solid of the respective extraction system and the effluent of the at least one continuous stirred tank extraction stage, and each extraction system further comprising a solid-liquid separator arranged in fluid communication with a last in series of the continuous stirred tank extraction stages of the respective extraction system and adapted to receive the effluent therefrom, wherein the solid-liquid separator is adapted and configured to separate the carbohydrate-depleted biomass solids, polar compound-depleted biomass solids, or spent biomass solids from the carbohydrate-containing liquid, the liquid polar organics fraction, or the rubber-containing non-polar solvent fraction.

2. A processing system for obtaining a rubber containing fraction from a rubber bearing plant comprising:
   (a) a first extraction system adapted and configured: to receive biomass from the plant or parts thereof and an organic polar solvent; to mix the biomass with an organic polar solvent in a manner such that the second extraction system generates a liquid polar organics fraction and polar compound-depleted biomass solids; and to separate the liquid polar organics fraction and polar compound-depleted biomass solids; and (b) a second extraction system adapted and configured to: receive the polar compound-depleted biomass solids from the first extraction system and a non-polar organic solvent; to mix the polar compound-depleted biomass solids with the non-polar organic solvent in a manner such that the second extraction system generates a rubber-containing non-polar solvent fraction and spent biomass solids; and to separate the rubber-containing non-polar solvent fraction and spent biomass solids;

wherein at least one of the first or second extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, the at least one continuous stirred tank extraction stage being adapted and configured to mix and form a homogeneous slurry, the homogeneous slurry corresponding to the solvent and solid of the respective extraction system and the effluent of the at least one continuous stirred tank extraction stage, and each extraction system further comprising a solid-liquid separator arranged in fluid communication with a last in series of the continuous stirred tank extraction stages of the respective extraction system and adapted to receive the effluent therefrom, wherein the solid-liquid separator is adapted and configured to separate the polar compound-depleted biomass solids or spent biomass solids from the liquid polar organics fraction or the rubber-containing non-polar solvent fraction.

3. The processing system of claim 2, further comprising solids conditioning and preparation machine(s) adapted and configured to reduce particle size, and/or alter the shape and condition of the solid material prior to introduction of the solid material into at least one continuous stirred tank extraction stage.

4. The processing system of claim 2, further comprising a recirculation loop associated with the at least one continuous stirred tank extraction stage.

5. The processing system of claim 4, wherein the recirculation loop includes a heat exchanger or heat transfer device.

6. The processing system of claim 4, wherein the recirculation loop includes a particle reduction and/or shape altering device.

7. The processing system of claim 2, wherein the at least one continuous stirred tank extraction stage has blades adapted and configured to increase shear to reduce and/or alter the particle size and shape of the biomass.

8. The processing system of claim 2, wherein at least one CSTE stage is adapted and configured to receive and contain the liquid solvent at a temperature of about 50° C. to about 100° C.

9. The processing system of claim 2, wherein at least one CSTE stage is adapted and configured to receive and contain the liquid solvent at a pressure that is greater than atmospheric pressure.

10. A method for extracting a rubber-containing non-polar solvent fraction from a rubber bearing plant, the method comprising:

(a) introducing into a first extraction system biomass from the plant or parts thereof and an organic polar solvent; mixing the biomass with the organic polar solvent to generate a liquid polar organics fraction and polar compound-depleted biomass solids, and separating the liquid polar organics fraction and polar compound-depleted biomass solids; wherein the rubber bearing plant is of the genus *Taraxacum* or is another non-*Hevea* plant;

(b) introducing into a second extraction system the polar compound-depleted biomass solids from the first extraction system and a non-polar organic solvent; mixing the polar compound-depleted biomass solids with the non-polar organic solvent to generate a rubber-containing non-polar solvent fraction and spent biomass solids; and separating the rubber-containing non-polar solvent fraction and spent biomass solids;

wherein at least one of the first or second extraction systems comprises a plurality of continuous stirred tank extraction stages arranged in fluid communication with each other in series such that effluent from one continuous stirred tank extraction stage flows to a next continuous stirred extraction stage in the series of the plurality of continuous stirred tank extraction stages of each extraction system, at least one of the continuous stirred tank extraction stages in each extraction system having an inlet adapted and configured to receive the solvent and an inlet adapted and configured to receive the biomass or the solids, the at least one continuous stirred tank extraction stage being adapted and configured to mix and form a homogeneous slurry, the homogeneous slurry corresponding to the solvent and solid of the respective extraction system and the effluent of the at least one continuous stirred tank extraction stage, and each extraction system further comprising a solid-liquid separator arranged in fluid communication with a last in series of the continuous stirred tank extraction stages of the respective extraction system and adapted to receive the effluent therefrom, wherein the solid-liquid separator is adapted and configured to separate the polar compound-depleted biomass solids or spent biomass solids from the liquid polar organics fraction, or the rubber-containing non-polar solvent fraction.

11. The method of claim 10, wherein the plant of the genus *Taraxacum* is *T. koksaghyz* or a cultivar thereof, a variety comprising introgressed germplasm from one or more *Taraxacum* species or cultivars, a variety comprising inter-specific hybrid germplasm, a variety comprising hybrid germplasm from two or more cultivars, a variety arising from mutagenesis or gene-editing of any rubber bearing *Taraxacum* species, cultivars, or variety, a transgenic *Taraxacum* plant, or any combination thereof.

12. The method of claim 10, wherein the liquid solvent is at a temperature of about 50° C. to about 100° C.

13. The method of claim 10, wherein the liquid solvent is at a pressure that is greater than atmospheric pressure.

14. The method of claim 10, further comprising drying the polar compound-depleted biomass solids or a portion thereof.

15. The method of claim 10, further comprising recirculating effluent associated with the at least one continuous stirred tank extraction stage and reducing a particle size and/or altering particle shape and/or shearing to expose the fibers of the solid material in the effluent during recirculating of the effluent.

16. The method of claim 10 further comprising recirculating effluent associated with the at least one continuous stirred tank extraction stage and altering the pressure and temperature of the effluent to increase a solubility of the product(s) in the solvent.

17. The method of claim 10, further comprising the step of filtering the polar organics fraction to separate fine solid particles after the solid-liquid separation.

18. The method of claim 10, further comprising at least one of the following steps of:
 (a) filtering the rubber-containing non-polar solvent fraction;
 (b) distilling and/or evaporating at least half of the non-polar organic solvent in the rubber-containing non-polar solvent fraction while maintaining the rubber in solution to obtain a concentrated rubber solution;
 (c) adding an anti-oxidant to a concentrated rubber solution;
 (d) adding cooled organic polar solvent to the concentrated rubber solution of (b) or (c) to precipitate the natural rubber;
 (e) further cooling the mixture of the organic polar solvent and non-polar organic solvent and precipitated rubber to form a gelatinous rubber precipitate and a mixed liquid organic solvent;
 (f) separating and removing the gelatinous rubber precipitate from the mixed liquid organic solvent;
 (g) forming and/or shaping the gelatinous rubber precipitate and/or further removing a portion of the mixed liquid organic solvent;
 (h) drying the formed and/or shaped gelatinous rubber precipitate to obtain a dried solid rubber product; or,
 (i) any combination of steps (a)-(h).

* * * * *